(12) United States Patent
Holbrooks et al.

(10) Patent No.: US 11,571,329 B2
(45) Date of Patent: Feb. 7, 2023

(54) PACKAGING SYSTEMS FOR IMPLANTABLE DEVICES AND RELATED METHODS

(71) Applicant: CooperSurgical, Inc., Trumbull, CT (US)

(72) Inventors: Ashley Holbrooks, New Haven, CT (US); Fabio Pinto, Stamford, CT (US); Patrick N. Gutelius, Monroe, CT (US); Derek R. Kulakowski, Oxford, CT (US); Gary Helstern, Newtown, CT (US); Richard I. Farrington, Waterbury, CT (US); John Triunfo, Fairfield, CT (US)

(73) Assignee: CooperSurgical, Inc., Trumbull, CT (US)

( * ) Notice: Subject to any disclaimer, the term of this patent is extended or adjusted under 35 U.S.C. 154(b) by 152 days.

(21) Appl. No.: 16/953,462

(22) Filed: Nov. 20, 2020

(65) Prior Publication Data
US 2021/0154045 A1    May 27, 2021

Related U.S. Application Data

(60) Provisional application No. 62/938,449, filed on Nov. 21, 2019.

(51) Int. Cl.
*A61F 6/00* (2006.01)
*A61F 6/18* (2006.01)
*A61F 6/14* (2006.01)

(52) U.S. Cl.
CPC ............... *A61F 6/18* (2013.01); *A61F 6/005* (2013.01); *A61F 6/144* (2013.01)

(58) Field of Classification Search
CPC ........................................................ A61F 6/005
(Continued)

(56) References Cited

U.S. PATENT DOCUMENTS 3,441,018 A    4/1969  Schneider
3,516,403 A    6/1970  Cournut
(Continued)

FOREIGN PATENT DOCUMENTS

FR    2 265 417         10/1975 ............ A61M 31/00
WO   WO 2017/013668    1/2017 ............... A61F 6/06

OTHER PUBLICATIONS

The International Preliminary Report on Patentability for International Application No. PCT/US2020/061428, dated Jun. 2, 2022.
(Continued)

*Primary Examiner* — Jacob K Ackun
(74) *Attorney, Agent, or Firm* — Fish & Richardson P.C.

(57) ABSTRACT

A tray for securing an implantable device to a carrier member includes a slot configured to retain the carrier member and a receptacle adjacent the slot. The carrier member surrounds a shaft of the implantable device. The receptacle has a first width at a proximal end of the receptacle to receive first and second arms of the implantable device in an initial state in which the first and second arms extend substantially perpendicularly from the shaft. The receptacle has a second width at a distal end of the receptacle for receiving the first and second arms of the implantable device in a collapsed state in which the first and second arms are folded against the shaft such that the carrier member can be slid over the first and second arms to retain the first and second arms. The second width is less than the first width.

20 Claims, 29 Drawing Sheets

(58) Field of Classification Search
USPC .................. 206/438, 363, 370, 564, 565
See application file for complete search history.

(56) References Cited

U.S. PATENT DOCUMENTS

| | | | |
|---|---|---|---|
| 3,522,803 | A | 8/1970 | Majzlin |
| 3,763,856 | A | 10/1973 | Blomberg |
| 3,771,520 | A | 11/1973 | Lerner |
| 3,783,861 | A | 1/1974 | Abramson |
| 3,805,777 | A | 4/1974 | Ansari |
| 3,857,391 | A | 12/1974 | Lerner |
| 3,880,156 | A | 4/1975 | Hoff |
| 3,889,666 | A | 6/1975 | Lerner |
| 3,918,444 | A | 11/1975 | Hoff et al. |
| 3,918,445 | A | 11/1975 | Okamoto et al. |
| 3,927,666 | A | 12/1975 | Hoff |
| 3,965,891 | A | 6/1976 | Lerner |
| 4,018,220 | A | 4/1977 | Emmett |
| 4,026,281 | A | 5/1977 | Mayberry et al. |
| 4,143,656 | A | 3/1979 | Holmes |
| 4,249,525 | A | 2/1981 | Krzeminski |
| 4,428,371 | A | 1/1984 | Krzeminski |
| 4,949,732 | A | 8/1990 | Spoon et al. |
| 5,370,129 | A * | 12/1994 | Diaz ................ A61F 6/18 128/839 |
| 5,785,053 | A | 7/1998 | Macandrew et al. |
| 5,842,474 | A * | 12/1998 | Blyskal ............. A61F 6/18 128/839 |
| 6,588,429 | B1 | 7/2003 | Wildemeersch |
| 6,709,667 | B1 | 3/2004 | Lowe et al. |
| 6,763,833 | B1 | 7/2004 | Khera et al. |
| 7,591,268 | B2 | 9/2009 | Lowe et al. |
| 7,661,429 | B2 | 2/2010 | Jjtila |
| 7,934,504 | B2 | 5/2011 | Lowe et al. |
| 8,381,733 | B2 | 2/2013 | Lowe et al. |
| 8,573,222 | B2 | 11/2013 | Weintraub |
| 8,584,679 | B2 | 11/2013 | Lowe et al. |
| 8,695,604 | B2 | 4/2014 | Lowe et al. |
| 9,265,651 | B2 | 2/2016 | Pandit |
| 9,308,119 | B2 | 4/2016 | Weintraub |
| 9,452,082 | B2 | 9/2016 | Lyytikäinen et al. |
| 9,492,311 | B2 | 11/2016 | Tal et al. |
| 9,492,312 | B2 | 11/2016 | Cappiello et al. |
| 9,597,224 | B2 | 3/2017 | Lowe et al. |
| 9,615,965 | B2 | 4/2017 | Lyytikäinen et al. |
| 9,668,912 | B2 | 6/2017 | Jutila et al. |
| 9,707,123 | B2 | 7/2017 | Lyytikäinen et al. |
| 9,949,817 | B2 | 4/2018 | Wesselmann et al. |
| 9,949,869 | B2 | 4/2018 | Tjäder et al. |
| 9,949,870 | B2 | 4/2018 | Frankenne et al. |
| 9,999,592 | B2 | 6/2018 | Duesterberg et al. |
| 10,028,858 | B2 | 7/2018 | Deckman et al. |
| 10,149,784 | B2 | 12/2018 | Jutila et al. |
| 10,532,025 | B2 | 1/2020 | Duesterberg et al. |
| 10,561,524 | B2 | 2/2020 | Lyytikäinen et al. |
| 10,583,035 | B2 | 3/2020 | Lyytikäinen et al. |
| 10,945,804 | B2 * | 3/2021 | Matityahu ......... A61B 17/1725 |
| 2007/0129734 | A1 | 6/2007 | Jutila |
| 2011/0162656 | A1 | 7/2011 | Jutila et al. |
| 2011/0166508 | A1 | 7/2011 | Lyytikäinen et al. |
| 2011/0172593 | A1 | 7/2011 | Lyytikäinen et al. |
| 2012/0111338 | A1 | 5/2012 | Weintraub |
| 2013/0068234 | A1 | 3/2013 | Pandit |
| 2013/0152942 | A1 | 6/2013 | Lyytikäinen et al. |
| 2013/0213406 | A1 | 8/2013 | Frankenne et al. |
| 2013/0220338 | A1 | 8/2013 | Lyytikäinen et al. |
| 2013/0255695 | A1 | 10/2013 | Jutila et al. |
| 2013/0319424 | A1 | 12/2013 | Weintraub |
| 2014/0041667 | A1 | 2/2014 | Cammack |
| 2014/0076328 | A1 | 3/2014 | Lyytikäinen et al. |
| 2014/0326249 | A1 | 11/2014 | Cappiello et al. |
| 2015/0114402 | A1 | 4/2015 | Lyytikäinen et al. |
| 2016/0262923 | A1 | 9/2016 | Ahola et al. |
| 2016/0361193 | A1 | 12/2016 | Lyytikäinen et al. |
| 2017/0027739 | A1 | 2/2017 | Deckman et al. |
| 2017/0196728 | A1 | 7/2017 | Lyytikäinen et al. |
| 2017/0239078 | A1 | 8/2017 | Jutila et al. |
| 2017/0273820 | A1 | 9/2017 | Deckman et al. |
| 2018/0014966 | A1 | 1/2018 | Lyytikäinen et al. |
| 2018/0055684 | A1 | 3/2018 | Lad et al. |
| 2018/0161196 | A1 | 6/2018 | Lyytikäinen et al. |
| 2018/0207023 | A1 | 7/2018 | Mehra et al. |
| 2018/0235804 | A1 | 8/2018 | Frankenne et al. |
| 2018/0303660 | A1 | 10/2018 | Deckman et al. |
| 2019/0231558 | A1 | 8/2019 | Beck et al. |
| 2019/0307600 | A1 | 10/2019 | Deckman et al. |
| 2020/0038232 | A1 | 2/2020 | Mikkonen et al. |
| 2020/0138623 | A1 | 5/2020 | Cappiello et al. |
| 2021/0030585 | A1 * | 2/2021 | Taparia ................. A61F 6/18 |
| 2021/0322146 | A1 * | 10/2021 | Rajpara .............. A61F 2/9525 |

OTHER PUBLICATIONS

The International Search Report and Written Opinion of the International Searching Authority for International Application No. PCT/US2020/061428, dated Mar. 9, 2021.
About Flexi-T website brochure, https://flexi-t.com/about-flexi-t/, (2019).
Ancora 375 Ag IUD website brochure, https://www.eurogine.com/item/en/1249-ancora-375-ag-iud-cu375+ag/, downloaded on Mar. 28, 2021.
Ancora 375 Cu IUD (Cu375) website brochure, https://www.eurogine.com/item/en/1250-ancora-375-cu-iud-cu375/, downloaded on Mar. 28, 2021.
China T 380A Iud Intrauterine Copper Contraceptive website brochure, https://finermed.en.made-in-china.com/print/lCkxaQHObtcF/China-T-380A-Iud-Intrauterine-Copper-Contraceptive.html, downloaded on Apr. 2, 2021.
Eurin Pharm Medical Devices website brochure, https://www.eurim.de/en/medical-devices, downloaded on Mar. 28, 2021.
GoldT IUD (Cu375+Au) website brochure, https://www.eurogine.com/item/en/1200-gold-t-iud-cu375+au/, downloaded on Mar. 28, 2021.
Wildemeersch, Dr. Dirk, "GyneFix insertion procedure", https://www.wildemeersch.com/products/gynefix/insertion-procedure/, (2021).
HLL Lifecare—T-CARE website brochure, www.lifecarehll.com/product/view/reference/eb160de1de89d9058fcb0b968dbbbd68hYCJ, (2018).
Intrauterine Contraceptive Device TT380A—Egemen International website brochure, https://egemenexport.en.ecplaza.net/products/intrauterine-contraceptive-device-tt380a_3973882, (1996).
Intrauterine device—All medical device manufacturers—Videos, https://www.medicalexpo.com/medical-manufacturer/intrauterine-device-3134.html, downloaded on Mar. 28, 2021.
Kyleena IUD website brochure, NDA 208224 Kyleena FDA Approved Mar. 1, 2018.
Laliberte UT380 Silver-Copper IUDs website brochure, (2021).
Liletta Brochure, (Oct. 2019).
Loading Devices—Hysterometer Instrument, IUD Loading Device website brochure, www.smbcorpn.com/smb-loading-devices.html, (2021).
MeltbeaGold, T-shaped gold-copper alloy intrauterine contraceptive medical device website brochure, downloaded on Mar. 28, 2021.
Mirena (levonorgestrel-releasing intrauterine system) website brochure, Initial U.S. Approval: 2000, downloaded on Mar. 28, 2021.
Multiload Cu250, Short Cu250 and Cu375 website brochure, mcs.open.ac.uk/nlg/old_projects/pills/corpus/PIL/data/Organon/Multiload/Multiload.html, downloaded on Mar. 28, 2021.
Shanghai Medical Suture Needle Factory Col. Ltd. Surgical Device website brochure, www.medsuture.com/English/news-detail.aspx?id=2, downloaded on Mar. 28, 2021.
Intra Uterine Contraception website brochure, www.durbin.co.uk, downloaded on Mar. 28, 2021.
SKYLA (levonorgestrel-releasing intrauterine system) website brochure, Initial U.S. Approval: 2000, downloaded on Mar. 28, 2021.
SMB Cu 375—Intrauterine Devices Manufacturers website brochure, www.smbcorpn.com/smb-cu-375.html, downloaded on Mar. 28, 2021.

(56) References Cited

OTHER PUBLICATIONS

SMB Tcu 380 Plus website brochure, www.smbcorpn.com/smb-copper-t-380-plus.html, downloaded on Mar. 28, 2021.
SMB Tcu 380Ag website brochure, www.smbcorpn.com/smb-copper-t-380-ag.html, downloaded on Mar. 28, 2021.
Beaton, C., "Why Does America Have Fewer Types of IUDs Than Other Countries?", *The Atlantic* (Apr. 18, 2017).
Yuan Gong Cu365 IUD website brochure, www.yuangong.com/products/htm/62.html, downloaded on Apr. 5, 2021.

* cited by examiner

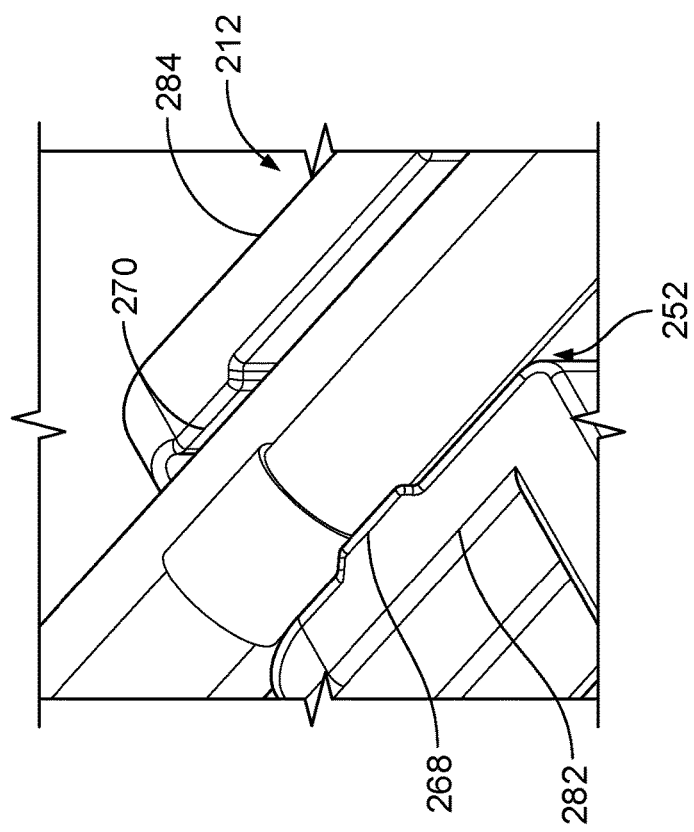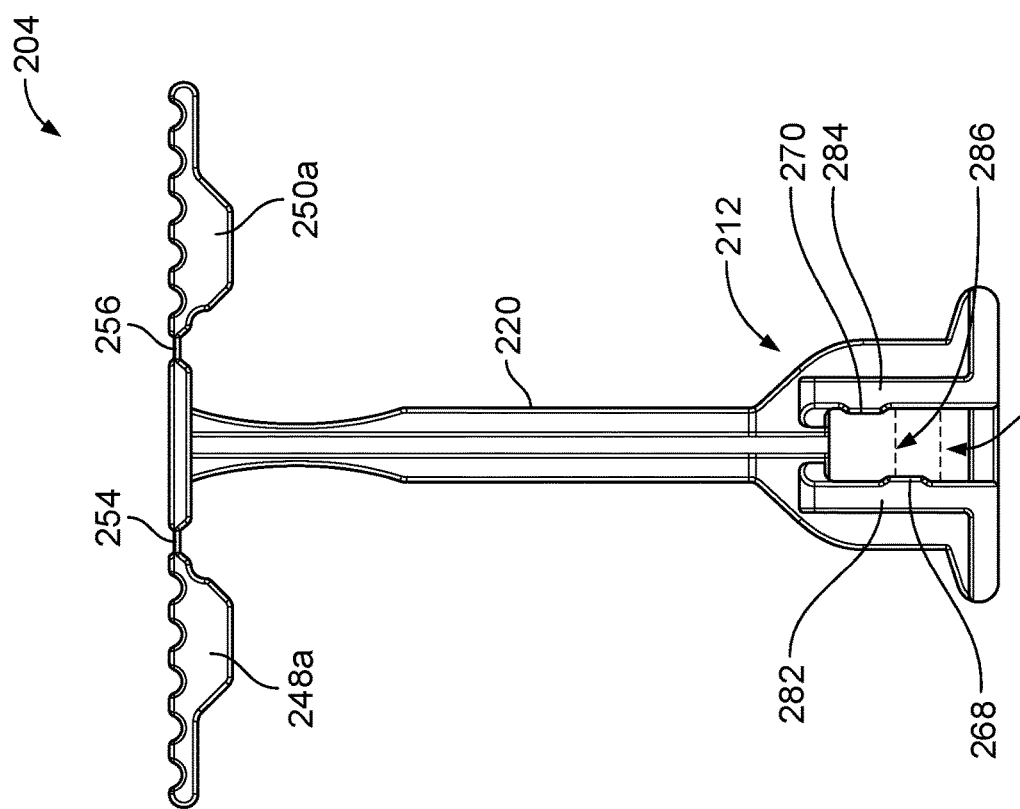

PACKAGING SYSTEMS FOR IMPLANTABLE DEVICES AND RELATED METHODS

CROSS-REFERENCE TO RELATED APPLICATIONS

This application claims priority to U.S. Provisional Patent Application No. 62/938,449, filed on Nov. 21, 2019. The entire content of this application is incorporated herein by reference.

TECHNICAL FIELD

This disclosure relates to packaging systems for implantable devices and related methods of handling such implantable devices using components of the packaging systems.

BACKGROUND

Intrauterine devices (IUDs) can be placed in the uterus of a patient as a form of contraceptive for preventing pregnancy. IUDs typically have a T-shape with arms extending perpendicularly to a shaft of the IUD. In some cases, to prepare an IUD for implantation, a healthcare provider must use his or her fingers to fold the arms of the IUD against the shaft and must maintain the arms in the folded configuration with his or her fingers while positioning an insertion tube over the arms in the folded configuration. However, due to the small size and surface area of the arms of the IUD, many healthcare providers have difficulty folding the arms using their fingers and maintaining the folded configuration of the arms long enough to pass the insertion tube over the arms of the IUD.

SUMMARY

This disclosure relates to packaging systems for implantable devices (e.g., IUDs) and related methods of handling such implantable devices using components of the packaging systems.

In one aspect, a loading device for securing an implantable device to a carrier member includes an elongate body configured to support the carrier member. The carrier member surrounds a shaft of the implantable device. The loading device further includes a first channel extending in a first direction from the elongate body and configured to receive a first arm of the implantable device that extends from the shaft and a second channel extending in a second direction from the elongate body and configured to receive a second arm of the implantable device that extends from the shaft, the second direction being opposite the first direction. The first and second channels are pivotable towards the elongate body respectively to move the first and second arms into a collapsed state against the shaft in which the first and second arms can be retained within the carrier member.

Embodiments may include one or more of the following features.

In some embodiments, the first and second channels are substantially perpendicular to the elongate body in an initial state or the first and second channels are positioned at an obtuse angle relative to the elongate body in an initial state.

In certain embodiments, the first and second channels are pivotable to fold the first and second arms into the collapsed state against the shaft to reduce a width of the implantable device such that the carrier member can further surround the first and second arms.

In some embodiments, the first and second channels are pivotable respectively at first and second hinges along the elongate body.

In certain embodiments, the implantable device is an intrauterine device, and the carrier member includes an insertion tube.

In some embodiments, the loading device further includes a receptacle extending from the elongate body and configured to retain the carrier member against the elongate body.

In certain embodiments, the receptacle includes flanges that are configured to retain the carrier member against the elongate body.

In some embodiments, the receptacle is configured to retain the carrier member in a slidable state against the elongate body.

In certain embodiments, the loading device further includes a string that can be pulled proximally to pivot the first and second channels towards the elongate body.

In some embodiments, the string is attached to a first end of the first channel and a second end of the second channel.

In certain embodiments, the string passes through the elongate body.

In another aspect, a method of preparing an implantable device for deployment includes accessing a loading device that is assembled with the implantable device and with a carrier member that surrounds a shaft of the implantable device. The loading device includes an elongate body supporting the carrier member, a first channel extending in a first direction from the elongate body and surrounding a first arm of the implantable device, and a second channel extending in a second, opposite direction from the elongate body and surrounding a second arm of the implantable device. The method further includes pivoting the first and second channels towards the elongate body respectively to move the first and second arms into a collapsed state against the shaft and placing the carrier member over the first and second arms to retain the first and second arms within the carrier member.

Embodiments may include one or more of the following features.

In some embodiments, sliding the carrier member over the first and second arms includes sliding the carrier member distally along the elongate body.

In certain embodiments, the loading device further includes a receptacle that extends from the elongate body and retains the carrier member against the elongate body.

In some embodiments, the method further includes lifting the carrier member, with the first and second arms of the implantable device retained therein, from the receptacle to remove the implantable device from the loading device.

In certain embodiments, the loading device further includes a string attached to a first end of the first channel and to a second end of the second channel.

In some embodiments, pivoting the first and second channels towards the elongate body respectively to move the first and second arms into a collapsed state against the shaft includes pulling the string proximally to pivot the first and second channels towards the elongate body.

In certain embodiments, the method further includes compressing a spring that abuts a proximal end of the loading device.

In some embodiments, the method further includes moving the loading device proximally against the spring.

In certain embodiments, the method further includes inserting the carrier member, carrying the implantable device with the first and second arms in the collapsed state, into a patient.

In some embodiments, the method further includes pulling the carrier member proximally with respect to the implantable device to release the first and second arms from the collapsed state.

In certain embodiments, the method further includes pushing the carrier member distally with respect to the implantable device to position the implantable device within the patient.

In some embodiments, the implantable device is an intrauterine device, and the carrier member includes an insertion tube.

In another aspect, a packaging system includes a loading device for securing an implantable device to a carrier member and a tray supporting the loading device. The loading device includes an elongate body configured to support the carrier member, the carrier member surrounding a shaft of the implantable device, a first channel extending in a first direction from the elongate body and configured to receive a first arm of the implantable device that extends from the shaft, and a second channel extending in a second direction from the elongate body and configured to receive a second arm of the implantable device that extends from the shaft, the second direction being opposite the first direction. The first and second channels are pivotable towards the elongate body respectively to move the first and second arms into a collapsed state against the shaft in which the first and second arms can be retained within the carrier member.

Embodiments may include one or more of the following features.

In some embodiments, the implantable device is an intrauterine device, and the carrier member includes an insertion tube.

In certain embodiments, the tray includes a first pair of flanges that secure the receptacle of the loading device to the tray.

In some embodiments, the tray includes a second pair of flanges that secure a distal end of the elongate body to the tray.

In certain embodiments, the tray defines a slot sized to accommodate the carrier member.

In some embodiments, the tray defines a inclined surface along which the first and second channels of the loading device can be pivoted.

In certain embodiments, the first and second channels are substantially perpendicular to the elongate body in an initial state.

In some embodiments, the first and second channels are pivotable to fold the first and second arms into the collapsed state against the shaft to reduce a width of the implantable device such that the carrier member can further surround the first and second arms.

In certain embodiments, the first and second channels are pivotable respectively at first and second hinges along the elongate body.

In some embodiments, the loading device further includes a receptacle extending from the elongate body and configured to retain the carrier member against the elongate body.

In certain embodiments, the receptacle includes flanges that are configured to retain the carrier member against the elongate body.

In some embodiments, the receptacle is configured to retain the carrier member in a slidable state against the elongate body In certain embodiments, the packaging system further includes a string that can be pulled proximally to pivot the first and second channels towards the elongate body.

In some embodiments, the string is attached to a first end of the first channel and a second end of the second channel.

In certain embodiments, the string passes through the elongate body.

In some embodiments, the system further includes a spring that abuts a proximal end of the elongate body.

In certain embodiments, compression of the spring in a proximal direction permits proximal movement of the loading device against the spring.

In another aspect, a tray for securing an implantable device to a carrier member includes a first slot configured to retain the carrier member, wherein the carrier member surrounds a shaft of the implantable device. The tray further includes a first receptacle adjacent the slot and having a first width to receive first and second arms of the implantable device in an initial state in which the first and second arms extend substantially perpendicularly from the shaft. The tray further includes a second receptacle adjacent the first receptacle and having a second width for receiving the first and second arms of the implantable device in a collapsed state in which the first and second arms are folded against the shaft such that the carrier member can be slid over the first and second arms to retain the first and second arms, the second width being less than the first width.

In another aspect, a method of preparing an implantable device for deployment includes accessing a tray that is assembled with the implantable device and a with a carrier member that surrounds a shaft of the implantable device. The tray includes a first slot configured to retain the carrier member, a first receptacle adjacent the slot and having a first width to receive first and second arms of the implantable device in an initial state in which the first and second arms extend substantially perpendicularly from the shaft, and a second receptacle adjacent the first receptacle and having a second width for receiving the first and second arms of the implantable device in a collapsed state in which the first and second arms are folded against the shaft. The method further includes moving the implantable device distally from the first receptacle into the second receptacle, causing the first and second arms of the implantable device to move from the initial state to the collapsed state, and sliding the carrier member distally along the first slot and over the first and second arms to retain the first and second arms within the carrier member.

In another aspect, a tray for securing an implantable device to a carrier member includes a slot configured to retain the carrier member and a receptacle adjacent the slot. The carrier member surrounds a shaft of the implantable device. The receptacle has a first width at a proximal end of the receptacle to receive first and second arms of the implantable device in an initial state in which the first and second arms extend substantially perpendicularly from the shaft. The receptacle has a second width at a distal end of the receptacle for receiving the first and second arms of the implantable device in a collapsed state in which the first and second arms are folded against the shaft such that the carrier member can be slid over the first and second arms to retain the first and second arms. The second width is less than the first width.

Embodiments may include one or more of the following features.

In some embodiments, the tray defines one or more flanges configured to secure the carrier member to the tray.

In certain embodiments, the tray includes a main body defining the slot and a loading aid defining the receptacle, the loading aid being coupled to a distal portion of the main body.

In some embodiments, the loading aid includes a first wall and a second wall opposite the first wall. The first and second walls are formed to guide the first and second arms of the implantable device into the collapsed state upon distal movement of the implantable device within the receptacle.

In certain embodiments, the receptacle has a tapered shape.

In some embodiments, the implantable device includes an intrauterine device, and the carrier member includes an insertion tube.

In certain embodiments, the receptacle is a first receptacle, and the tray further defines a second receptacle adjacent the slot and opposite the first receptacle, the second receptacle being configured to receive a handle that is coupled to the carrier member In some embodiments, the second receptacle is longer than the handle to permit distal movement of the handle within the second receptacle.

In certain embodiments, the tray further defines a gripping region positioned along the slot, the gripping region being wider than the slot.

In some embodiments, the tray includes ruler markings adjacent the gripping region, the ruler markings indicating respective uterine depths.

In certain embodiments, the tray includes a first support body defining the receptacle and a second support body slidably coupled to the first support body.

In some embodiments, the first support body defines an elongate platform slidably coupled to the second support body and a shoulder configured to prevent distal movement of the second support body relative to the first support body beyond the shoulder.

In certain embodiments, distal movement of the second support body relative to the first support body causes the implantable device to move distally within the receptacle from the proximal end of the receptacle to the distal end of the receptacle to cause the first and second arms of the implantable device to move from the initial state into the collapsed state.

In another aspect, a packaging system includes a tray for securing an implantable device to a carrier member and a protective cover formed complementary to at least a portion of the tray for securing a handle that is coupled to the carrier member to the tray. The tray includes a slot configured to retain the carrier member and a receptacle adjacent the slot. The carrier member surrounds a shaft of the implantable device. The receptacle has a first width at a proximal end of the receptacle to receive first and second arms of the implantable device in an initial state in which the first and second arms extend substantially perpendicularly from the shaft. The receptacle has a second width at a distal end of the receptacle for receiving the first and second arms of the implantable device in a collapsed state in which the first and second arms are folded against the shaft such that the carrier member can be slid over the first and second arms to retain the first and second arms. The second width is less than the first width.

Embodiments may include one or more of the following features.

In some embodiments, the tray defines one or more flanges configured to secure the carrier member to the tray.

In certain embodiments, the tray includes a main body defining the slot and a loading aid defining the receptacle, the loading aid being coupled to a distal portion of the main body.

In some embodiments, the loading aid includes a first wall and a second wall opposite the first wall. The first and second walls are formed to guide the first and second arms of the implantable device into the collapsed state upon distal movement of the implantable device within the receptacle.

In certain embodiments, the receptacle has a tapered shape.

In some embodiments, the tray further defines a gripping region positioned along the slot, the gripping region being wider than the slot.

In another aspect, a method of preparing an implantable device for deployment includes accessing a tray that is assembled with the implantable device and with a carrier member that surrounds a shaft of the implantable device. The tray defines a slot configured to retain the carrier member and a receptacle adjacent the slot. The carrier member surrounds a shaft of the implantable device. The receptacle has a first width at a proximal end of the receptacle to receive first and second arms of the implantable device in an initial state in which the first and second arms extend substantially perpendicularly from a shaft of the implantable device. The receptacle has a second width at a distal end of the receptacle for receiving the first and second arms of the implantable device in a collapsed state in which the first and second arms are folded against the shaft. The second width is less than the first width. The method further includes moving the implantable device distally from the proximal end of the receptacle to the distal end of the receptacle, causing the first and second arms of the implantable device to move from the initial state to the collapsed state, and sliding the carrier member distally along the slot and over the first and second arms to retain the first and second arms within the carrier member.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 5 is a front view of the loading device of FIG. 4.

FIG. 6 is an enlarged perspective view of a portion of the loading device of FIG. 4.

DETAILED DESCRIPTION

Figure 1:
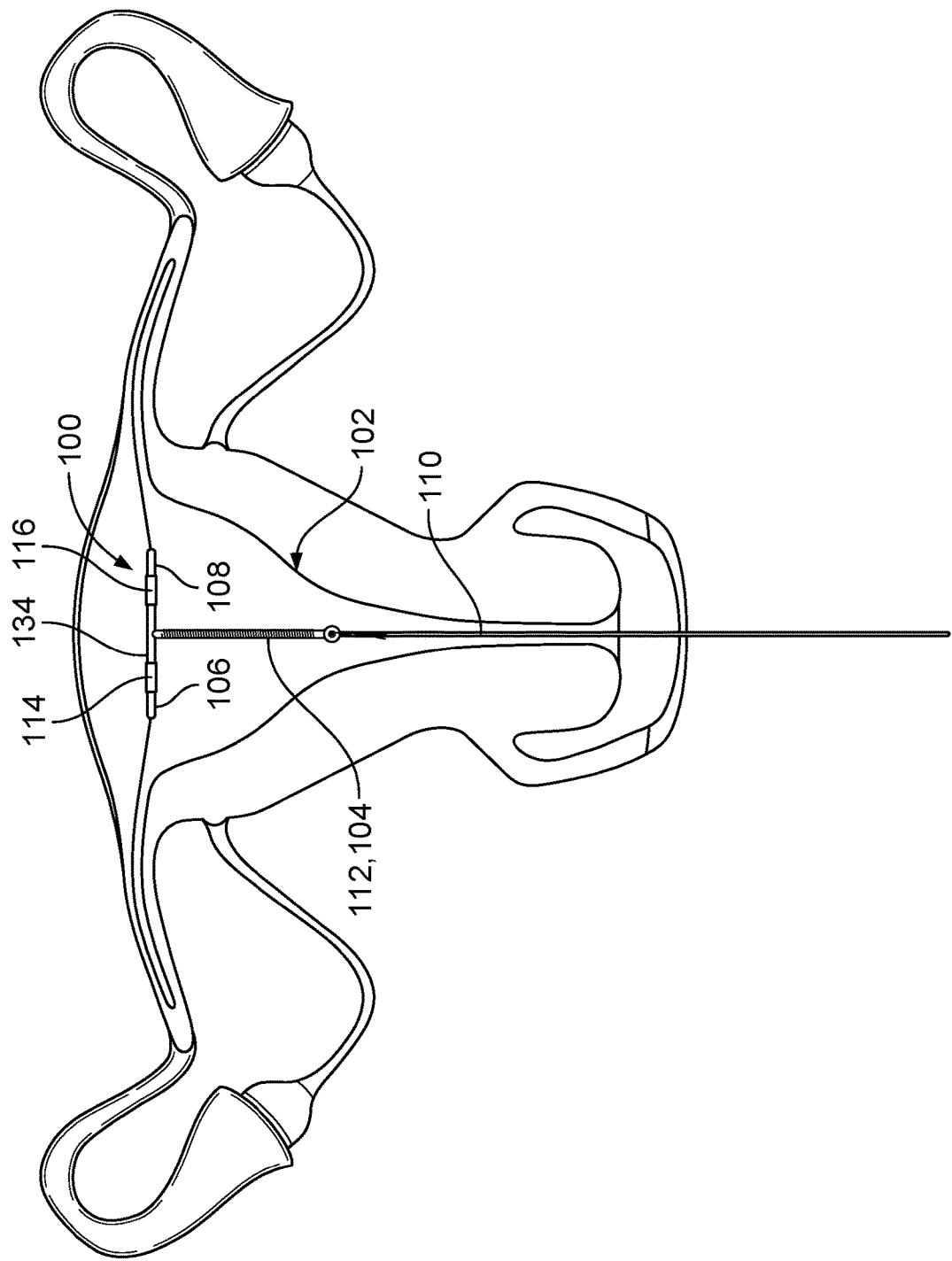
FIG. 1 is a perspective view of an intrauterine device (IUD) positioned in a uterus of a patient.

FIG. 1 illustrates an intrauterine device (IUD) 100 positioned within a uterus 102 of a patient. When implanted in the uterus 102 of the patient, the IUD 100 acts as a contraceptive device for preventing pregnancy. The IUD 100 includes a shaft 104 and a pair of arms 106, 108 extending from the shaft 104. As shown in FIG. 1, when the IUD 100 is properly positioned within the uterus 102, the arms 106, 108 of the IUD 100 are substantially perpendicular to the shaft 104 and are positioned along a wall (e.g., a fundus) of the uterus 102.

The IUD 100 also includes a copper wire 112 that is secured to the shaft 104 and copper collars 114, 116 that are respectively secured to the arms 106, 108 of the IUD 100. For example, the copper wire 112 and copper collars 114, 116 can release copper into the uterus 102, where such copper functions as a contraceptive to prevent pregnancy in the patient. The IUD 100 can remain in the uterus 102 for an extended period (e.g., up to about 10 years) and provides continuous contraception while the IUD 100 is positioned within the uterus 102.

The IUD 100 also includes one or more threads 110 extending from an end of the shaft 104 that is opposite from the arms 106, 108. The threads 110 can be manipulated to remove the IUD 100 from the uterus 102. In some examples, the threads 110 are trimmed to a shorter length following implantation of the IUD 100 in the uterus 102. In some examples, the shaft 104 of the IUD 100 has a length of about 3.1 cm to about 3.3 cm (e.g., about 3.20 cm) and a diameter of about 0.14 cm to about 0.17 cm (e.g., about 0.152 cm). In some examples, each of the arms 106, 108 of the IUD 100 has a length of about 1.52 cm to about 1.53 cm (e.g., about 1.524 cm) and a diameter of about 0.15 cm to about 0.17 cm (e.g., about 0.157 cm). Example materials from which the IUD 100 may be made include polypropylene and copper.

Figure 2:
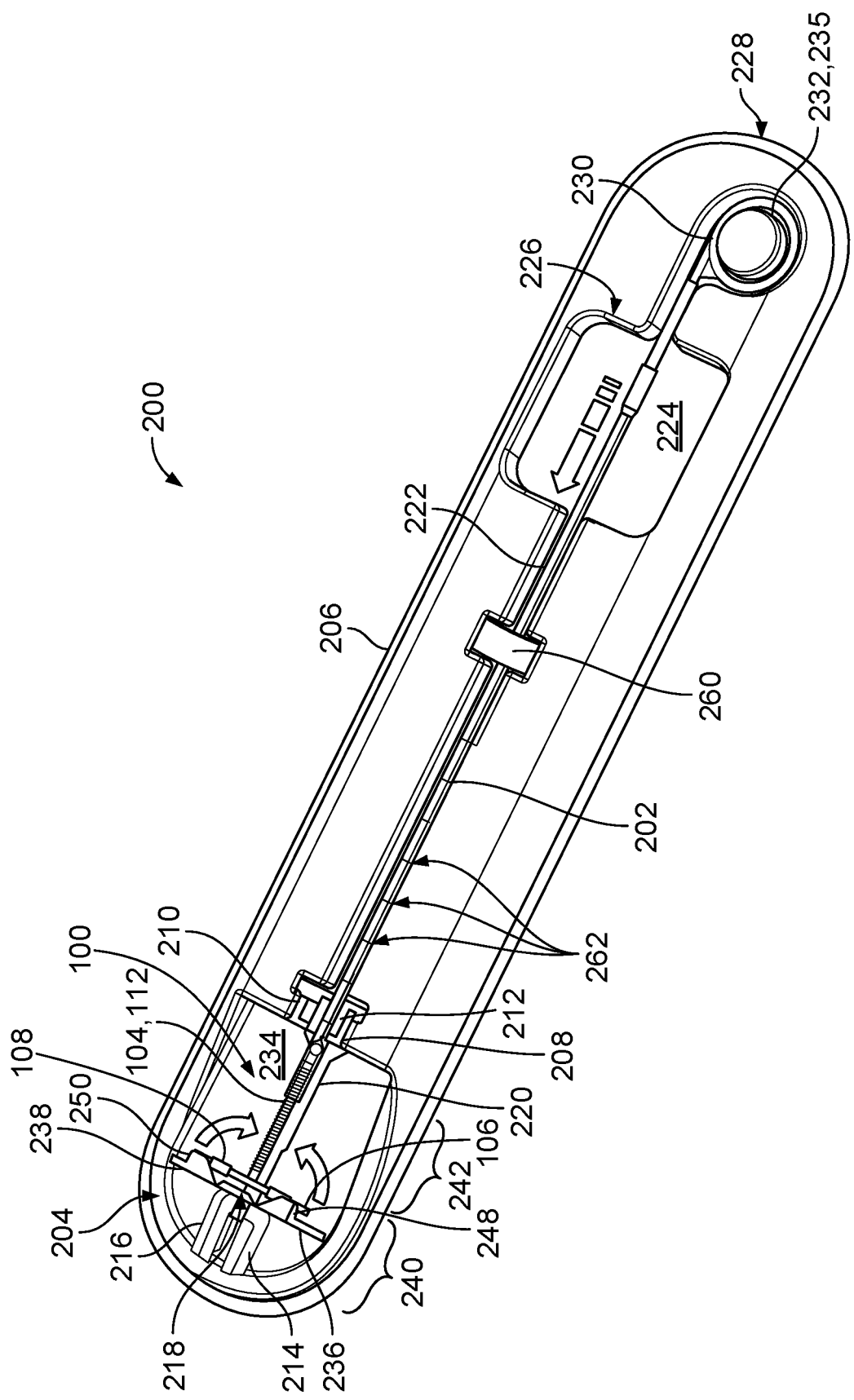
FIG. 2 is a perspective view of a portion of a packaging system that houses the IUD of FIG. 1 and an insertion tube.
Figure 3:
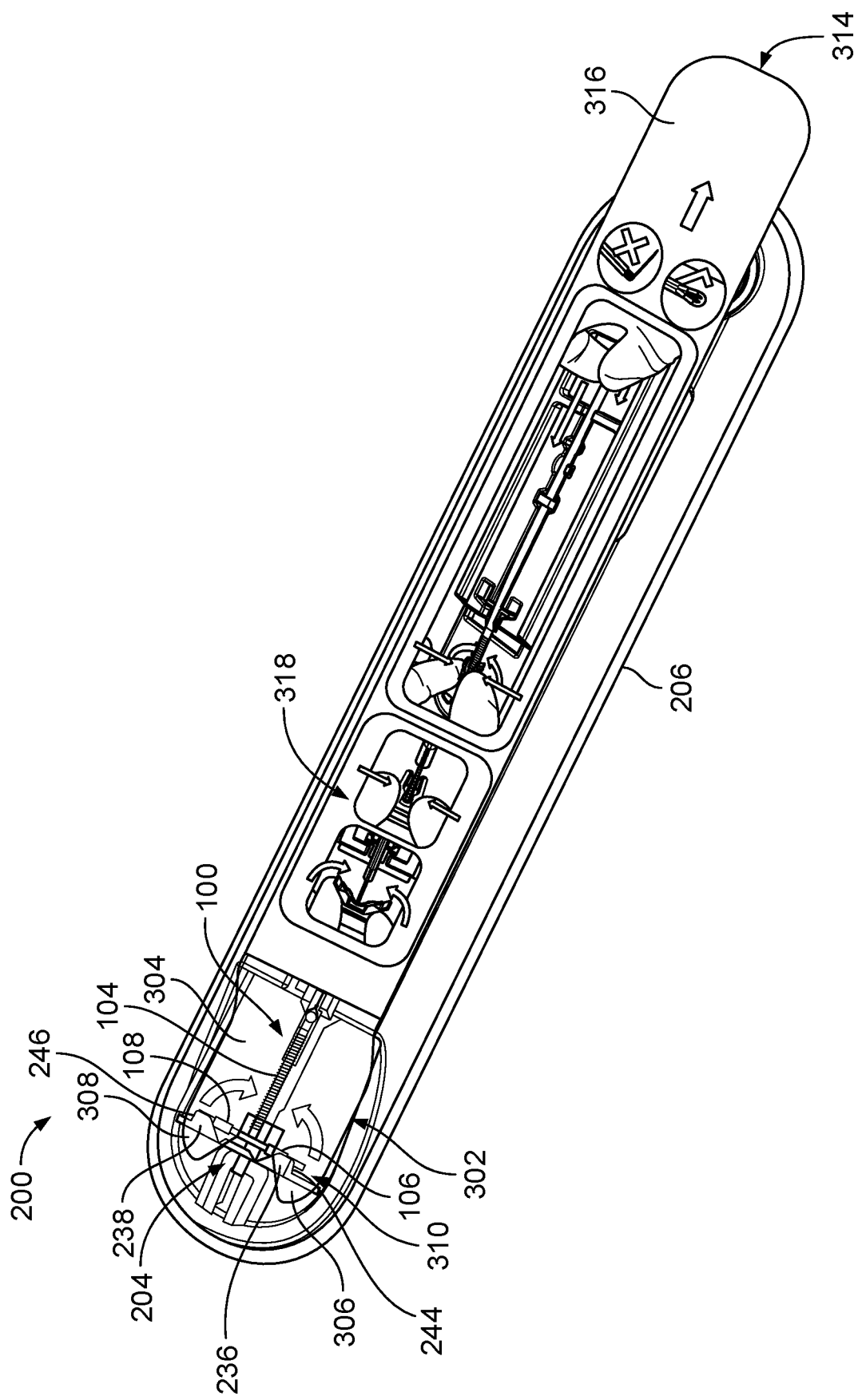
FIG. 3 is a perspective view of a portion of the packaging system of FIG. 2.

FIGS. 2 and 3 illustrate a packaging system 200 that houses the IUD 100 and an insertion tube 202 that can be used to implant the IUD 100 within the uterus 102 the patient. The insertion tube 202 is marked with ruled markings 262 and is equipped with a movable indicator 260, as will be discussed in more detail below. The packaging system 200 also houses a rod 235 that is positioned within the insertion tube 202 and that is used to implant the IUD 100, which also be discussed in more detail below.

The packaging system 200 includes a tray 206, a loading device 204 that is secured to the tray 206, and a lid (not shown) that covers the tray 206. The loading device 204 can be used to secure the IUD 100 to the insertion tube 202 for implanting the IUD 100 within the uterus 102 of the patient.

The loading device 204 includes an elongate body 220, a receptacle 212 that extends from one end of the elongate body 220, and two arms 236, 238 that extend substantially perpendicular from an opposite end of the elongate body 220 in an initial configuration, as will be discussed in more detail below with respect to FIGS. 4-6. The tray 206 includes a first pair of flanges 208, 210 that secure the receptacle 212 of the loading device 204 to the tray 206 and a second pair of flanges 214, 216 that secure a distal end 218 of the elongate body 220 of the loading device 204 to the tray 206 in a pre-packaged configuration. The loading device 204 can be removed from the tray 206 without damaging the loading device 204 or the tray 206.

As depicted in FIG. 2, the tray 206 defines a slot 222 that accommodates the insertion tube 202. The slot 222 is sized to allow the insertion tube 202 to move axially within the slot 222 along the length of the slot 222 and to substantially restrict lateral movement the insertion tube 202 within the slot 222. The slot 222 also defines opposing flanges 290, 292 (shown in FIG. 9) that narrow an opening of the slot 222 to prevent the insertion tube 202 from popping out of the slot 222. In some examples, the slot 222 has a length of about 2.7 cm to about 3.1 cm (e.g., about 2.90 cm), a width of about 0.48 cm to about 0.53 cm (e.g., about 0.51 cm), and a depth of about 0.63 cm to about 0.68 cm (e.g., about 0.66 cm).

The tray 206 further defines a recessed region 224 along the slot 222 that provides space for a user's fingers to access (e.g., grip) the insertion tube 202. For example, a healthcare provider can grasp a portion of the insertion tube 202 positioned within the gripping region 224 with his or her fingers and slide the insertion tube 202 distally along the slot 222 over folded arms 106, 108 of the IUD 100, as will be discussed in more detail below with respect to FIGS. 9 and 10. In some examples, the gripping region 224 defined within the tray 206 has a length of about 4.2 cm to about 4.4 cm (e.g., about 4.31 cm), a width of about 3.9 cm to about 4.1 cm (e.g., about 4.00 cm), and a depth of about 0.9 cm to about 1.0 cm (e.g., about 0.95 cm). In some examples, a proximal end 226 of the gripping region 224 is positioned about 5.2 cm to about 5.4 cm (e.g., about 5.27 cm) apart from a proximal end 228 of the tray 206.

The tray 206 further defines a circular depression 230 adjacent the slot 222 and adjacent the proximal end 228 of the tray 206. The circular depression 230 accommodates a circular end portion 232 of a rod 235 that extends within the insertion tube 202 from the end portion 232 to a proximal end of the shaft 104 of the IUD. The rod 235 is used to assist with positioning the IUD 100 within the uterus 102. In some examples, the circular depression 230 defined within the tray 206 has an outer diameter of about 2.2 cm to about 2.4 cm (e.g., about 2.26 cm), a depth of about 0.5 cm to about 0.7 cm (e.g., about 0.58 cm), and a width (e.g., the distance from an outer wall of the circular depression 230 to an inner wall of the circular depression 230) of about 0.2 cm to about 0.4 cm (e.g., about 0.27 cm).

Still referring to FIG. 2, the tray 206 also defines a inclined surface 234 that supports the loading device 204. The inclined surface 234 provides a recessed region that allows for pivoting of the arms 236, 238 of the loading device 204 in order to fold the arms 106, 108 of the IUD 100 inward, as will be discussed in more detail below with respect to FIGS. 4-8. The inclined surface 234 includes an upper portion 240 and a lower portion 242. The upper portion 240 of the inclined surface 234 has a generally semicircular shape, and the lower portion 242 of the inclined surface 234 has a generally rectangular shape. In some examples, the lower portion 242 of the inclined surface 234 has a length of about 5.3 cm to about 5.5 cm (e.g., about 5.39 cm) and a width of about 4.4 cm to about 4.7 cm (e.g., about 4.56 cm). In some examples, the lower portion 242 is oriented at an angle of about 164 degrees to about 174 degrees (e.g., about 169 degrees) with respect to the upper portion 240.

The tray 206 is typically made of one or more polymer materials. Example materials from which the tray 206 can be made include polystyrene, polypropylene, and PETG (polyethylene terephthalate glycol), ABS (acrylonitrile butadiene styrene), HDPE (high density polyethylene), LDPE (low density polyethylene). Example processes for forming the tray 206 include injection molding, vacuum forming, pressure forming, and die cut cards. In some examples, the tray 206 has a total length of about 28.3 cm to about 29.9 cm (e.g., about 29.1 cm), a total width of about 22.6 cm to about 24.2 cm (e.g., about 23.4 cm), and a total height of about 0.9 cm to about 1.1 cm (e.g., about 0.98 cm).

Referring to FIG. 3, the packaging system 200 also may include an insert 302 for helping to retain the IUD 100 against the loading device 204. The insert 302 includes a proximal body 316, a distal body 304, and a pair of projections 306, 308 extending from a distal end 310 of the distal body 304. The insert 302 helps prevent movement and dislodgement of the IUD 100 from the loading device 204 during transit of the packaging system 200 and prior to preparation of the IUD 100 for implantation. The arms 106, 108 of the IUD 100 are positioned within channels 244, 246 defined by the arms 236, 238 of the loading device 204. The distal body 304 of the insert 302 can be positioned over the shaft 104 of the IUD 100, and each of the projections 306, 308 of the insert 302 can be positioned under a respective arm 106, 108 of the IUD 100 to prevent the arms 106, 108 from sliding out of the channels 244, 246 prior to preparation of the IUD 100 for implantation. The insert 302 is removed from the tray 206 prior to preparing the IUD 100 for implantation to allow for movement and folding of the arms 106, 108 of the IUD 100. For example, the insert 302 can be removed from the tray 206 by pulling proximally on a proximal end 314 of the proximal body 316 to slide the insert 302 proximally away from the loading device 204 and thus slide the projections 306, 308 of the insert 302 out from under the arms 106, 108 of the IUD 100.

The insert 302 can include one or both of written and graphical instructions 318 for preparing the IUD 100 for implantation. As shown in FIG. 3, the instructions 318 for preparing the IUD 100 may be printed on the proximal body 316 of the insert 302, or in other cases, the instructions 318 may be printed on the distal body 304 of the insert 302

The insert 302 is typically transparent in appearance. For example, either or both of the proximal body 316 and the distal body 304 of the insert 302 is typically made of one or more plastic materials, such as high impact polystyrene (HIPS), polyethylene terephthalate glycol, acrylonitrile butadiene styrene (ABS), high density polyethylene (HDPE), or one or more paper materials. In some examples, the insert 302 is manufactured using one or more processes, such as thermoforming, die-cutting and injection molding and heat staking. The distal and proximal bodies 304, 316 of the insert 302 typically have a combined length of about 27.0 cm to about 27.3 cm (e.g., about 27.13 cm), a width of about 4.2 cm to about 4.4 cm (e.g., about 4.32 cm), and a thickness of about 0.03 cm to about 0.05 cm (e.g., about 0.04 cm). Each of the projections 306, 308 typically has a length of about 1.3 cm to about 1.5 cm (e.g., about 1.44 cm), a width of about 1.4 cm to about 1.6 cm (e.g., about 1.51 cm), and a thickness of about 0.03 cm to about 0.05 cm (e.g., about 0.04 cm).

Figure 4:
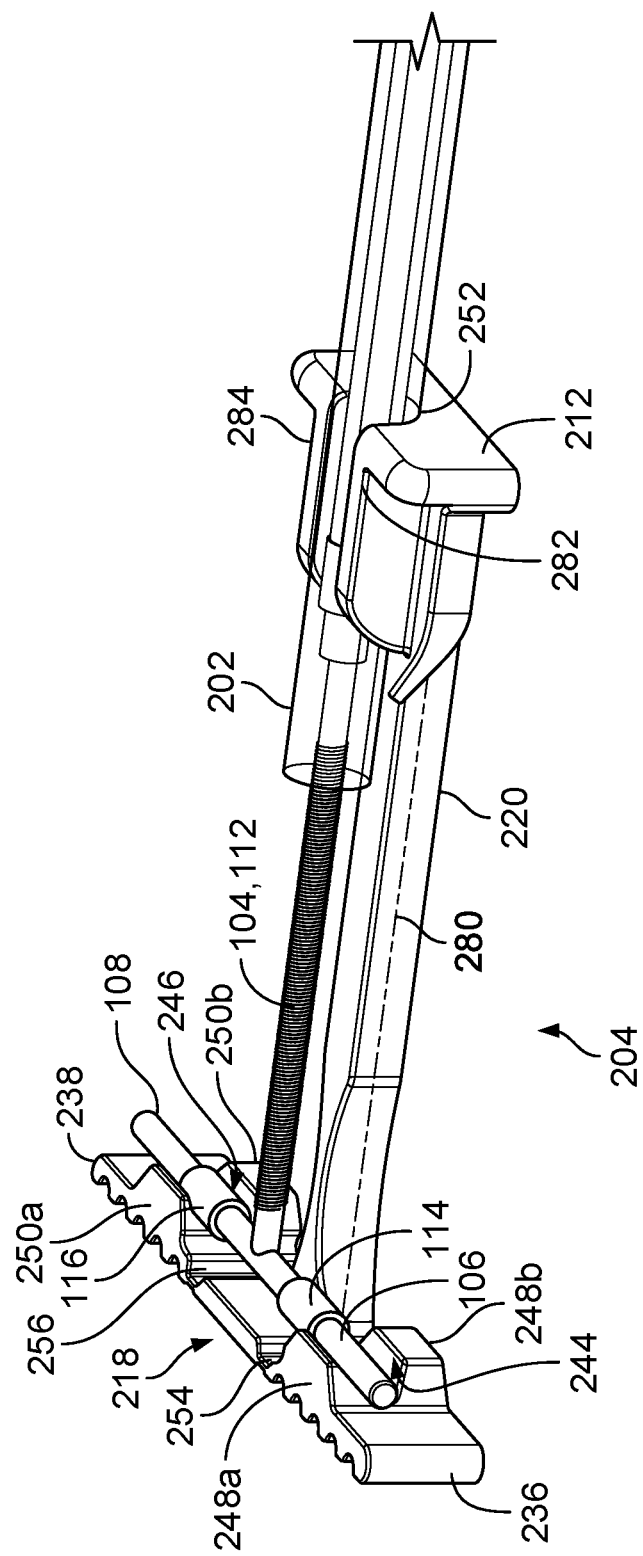
FIG. 4 is a perspective view of a loading device of the packaging system of FIG. 2.

FIGS. 4-6 illustrate various views of the loading device 204 for securing the IUD 100 to the insertion tube 202. As depicted in FIGS. 4 and 5, the loading device 204 is generally T-shaped. As described above with respect to FIG. 2, the loading device 204 includes the elongate body 220, the arms 236, 238, and the receptacle 212. The elongate body 220 extends along the length of the shaft 104 of the IUD 100. The pair of arms 236, 238 extend from the distal end 218 of the elongate body 220, and the receptacle 212 is positioned at the end of the elongate body 220, opposite the arms 236, 238, as discussed above. In some examples, the elongate body 220 has a maximum width of about 0.2 cm to about 0.5 cm (e.g., about 0.44 cm) and a length of about 1.9 cm to about 9.5 cm (e.g., about 3.25 cm).

The arms 236, 238 respectively extend from the distal end 218 of the elongate body 220 at flexible locations 254, 256 (e.g., hinges). As depicted in FIGS. 4 and 5, the arms 236, 238 are each substantially perpendicular to the elongate body 220 in an initial configuration (e.g., in a packaged state). In some embodiments, the arms 236, 238 are positioned at an obtuse angle with respect to the elongate body 220. For example, the arms 236, 238 are typically oriented at an angle about 90 degrees to about 120 degrees (e.g., about 90 degrees) relative to a longitudinal axis 280 of the elongate body 220 in the initial configuration. In some examples, each arm 236, 238 has a total width of about 0.02 cm to about 0.50 cm (e.g., about 0.19 cm), a length of about 2.1 cm to about 2.3 cm (e.g., about 2.18 cm), and a total height of about 0.5 cm to about 1.0 cm (e.g., about 0.72 cm). The arms 236, 238 provide relatively large contact surfaces (e.g., the upper surfaces of the arms 236, 238) for the user's fingers as compared to surfaces of the arms 106, 108 of the IUD 100. The large contact surfaces of the arms 236, 238 provide gripping regions that facilitate manipulation of the arms 106, 108 by the user, as compared to manipulation of the arms 106, 108 by conventional means of direct contact with the arms 106, 108.

The arms 236, 238 respectively define channels 244, 246 along the lengths of the arms 236, 238. As depicted in FIG. 4, the channels 244, 246 respectively surround the arms 106, 108 of the IUD 100 when the IUD 100 is positioned on the loading device 204 in the packaged state. The arm 236 includes flanges 248a, 248b that in part define the channel 244. Similarly, the arm 238 includes flanges 250a, 250b that in part define the channel 246. With the proximal end of the shaft 104 supported by the rod 235 and the insertion tube 202, and with the arms 106, 108 positioned within the channels 244, 246, a position of the IUD 100 is substantially maintained along the loading device 204 with limited movement during preparation of the IUD 100 for implantation, which will be discussed in more detail below. Furthermore, the channels 244, 246 are sized such that the arms 106, 108 of the IUD 100 can be easily released from the channels 244, 246 when necessary during preparation of the IUD 100 for implantation, as will be discussed in more detail below. As shown in FIG. 4, the arms 106, 108 extend past ends of the channels 244, 246. In some examples, each of the channels 244, 246 has a width of about 0.9 cm to about 1.0 cm (e.g., about 0.94 cm), a height of about 0.4 cm to about 0.5 cm (e.g., about 0.42 cm), and a depth of about 0.2 cm to about 0.3 cm (e.g., about 0.28 cm).

As depicted in FIGS. 4 and 5, each of the arms 236, 238 are pivotably attached to the elongate body 220 by a respective flexible location 254, 256. The flexible locations 254, 256 permit the arms 236, 238 to pivot radially inward towards the elongate body 220. For example, the flexible locations 254, 256 allow the arms 236, 238 to be moved between a position substantially perpendicular to the elongate body 220 and a position substantially parallel to the elongate body 220. When sufficient rotationally directed forces are applied to the arms 236, 238, the flexible locations 254, 256 deform to permit the arms 236, 238 to fold inward towards the elongate body 220. The flexible locations 254, 256 are flexible such that the flexible locations 254, 256 can remain functional (e.g., substantially mechanically intact) over multiple pivoting movements of the arms 236, 238 (e.g., such that the arms 236, 238 can be pivoted at least three times while the flexible locations 254, 256 remain intact). In some examples, each of the flexible locations 254, 256 has a width of about 0.1 cm to about 0.2 cm (e.g., about 0.16 cm), a height of about 0.7 cm to about 1.0 cm (e.g., about 0.72 cm), and a thickness of about 0.02 cm to about 0.06 cm (e.g., about 0.04 cm).

The receptacle 212 defines a channel 252 that supports the insertion tube 202. For example, the channel 252 is formed to prevent the insertion tube 202 from falling out or otherwise becoming dislodged from the receptacle 212 during transportation of the packaging system 200. The channel 252 is sized to permit the insertion tube 202 to slide axially within the channel 252 while restricting lateral movement of the insertion tube 202. For example, a healthcare provider can use his or her fingers to slide the insertion tube 202 along the channel 252 of the receptacle 212 to cover ends of the arms 236, 238 of the IUD 100 when the arms 236, 238 are in a folded state, as will be discussed in more detail below. The channel 252 is sized and shaped such that the insertion tube 202 can be detached from the loading device 204 without damaging the insertion tube 202 or the loading device 204. For example, the insertion tube 202 can be pulled upward from the receptacle 212 to remove the insertion tube 202 from the loading device 204 when needed. In some examples, the channel 252 has an interior width of about 0.4 cm to about 0.5 cm (e.g., about 0.45 cm), a length of about 1.1 cm to about 1.3 cm (e.g., about 1.19 cm), and a depth of about 0.4 cm to about 0.5 cm (e.g., about 0.45 cm).

As depicted in FIGS. 4-6, the channel 252 is defined by a pair of flanges 282, 284 on the receptacle 212. The flanges 282, 284 define an elongate opening 286 of the channel 252 that is narrower than a width of the insertion tube 202, such that the flanges 282, 284 retain the insertion tube 202 within the channel 252 during transit and preparation of the IUD 100 for implantation. In some examples, each of the flanges 282, 284 of the receptacle 212 has a width (excluding protrusions 268, 270) of about 0.1 cm to about 0.3 cm (e.g., about 0.20 cm), a length of about 0.9 cm to about 1.1 cm (e.g., about 1.01 cm), and a height of about 0.3 cm to about 0.4 cm (e.g., about 0.37 cm). In some examples, the elongate opening 286 has a width of about 0.4 cm to about 0.5 cm (e.g., about 0.45 cm).

The flanges 282, 284 respectively define protrusions 268, 270 along the elongate opening 286 of the channel 252 that help to retain the insertion tube 202 in the channel 252. As depicted in FIG. 6, the protrusions 268, 270 are offset from each other along the length of the channel 252. In some examples, each of the protrusions 268, 270 has a length of about 0.2 cm to about 0.4 cm (e.g., about 0.3 cm), and axial centers of the protrusions 268, 270 are offset from each other by a distance of about 0.1 cm to about 0.4 cm (e.g., about 0.39 cm).

The loading device 204 is typically made of one or more materials that are sufficiently compliant and resistant to plastic deformation to allow for repeated bending of the flexible locations 254, 256. For example, such materials may behave more rigidly in a relatively thicker cross section of the elongate body 220 and behave more elastically in a relatively thinner cross sections at the flexible locations 254, 256. Accordingly, the loading device 204 is typically made of one or more polymer materials, such as polypropylene, polyethylene, and thermoplastic elastomers (e.g., vulcanized ethylene propylene diene monomer (EPDM) rubber). Example processes for manufacturing the loading device 204 include injection molding, plastic machining, and 3D printing.

FIGS. 7-11 illustrate a method of securing the IUD 100 to the insertion tube 202 using the packaging system 200. As previously discussed, the IUD 100 is packaged with the arms 106, 108 within the channels 244, 246 of the arms 236, 238 of the loading device 204 and with the shaft 104 extending into the insertion tube 202. The insertion tube 202 is itself secured in the receptacle 212 of the loading device 204 and in the slot 222 of the tray 206, and the rod 235 extends within the insertion tube 202 to the proximal end of the shaft 104 of the IUD 100.

Figure 7:
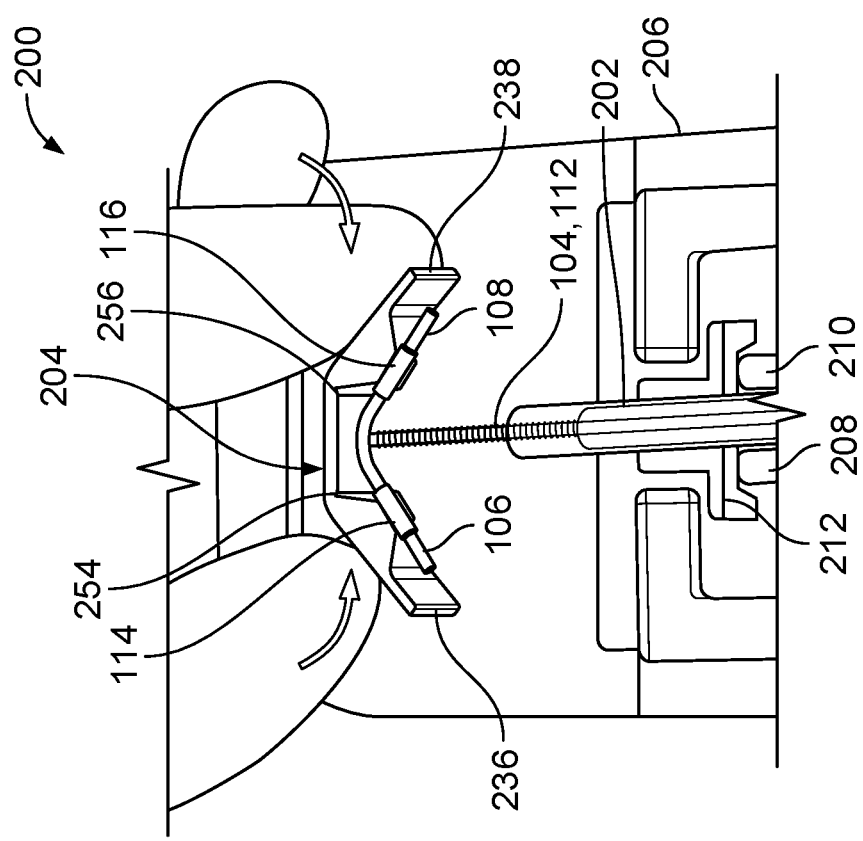

Referring to FIG. 7, a user (e.g., a healthcare provider) can use his or her fingers to push the arms 236, 238 of the loading device 204 (e.g., with the arms 106, 108 of the IUD 100 positioned therein) inwards towards the elongate body 220 to fold the arms 106, 108 towards the shaft 104 of the IUD 100.

Figure 8:
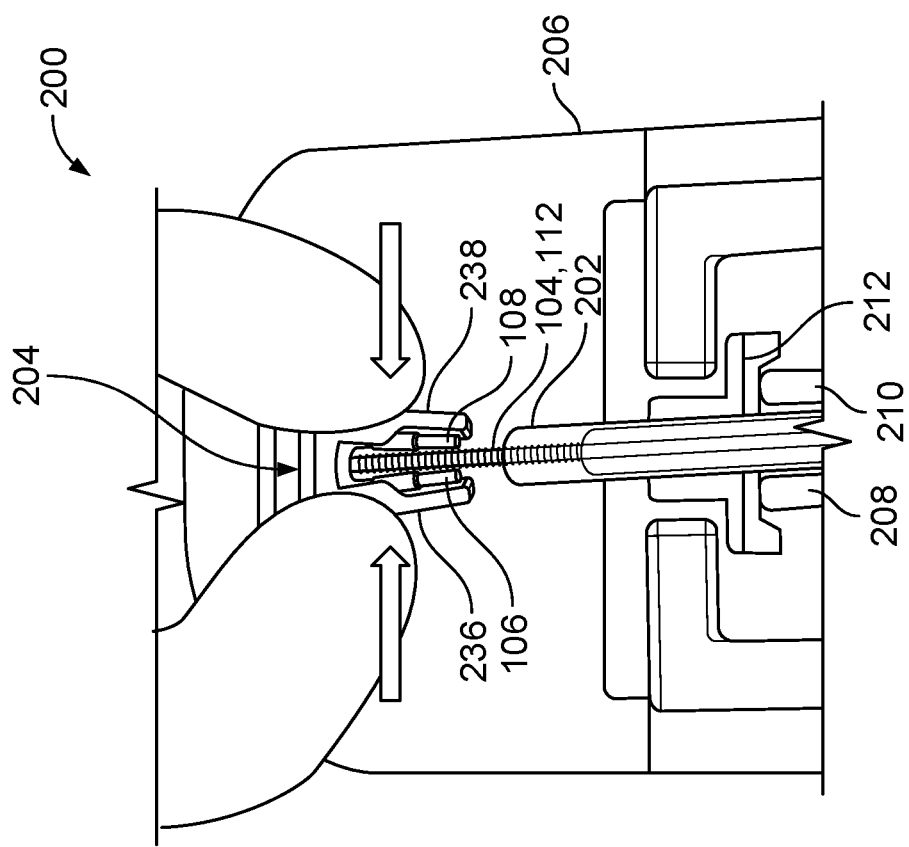
FIGS. 7-11 illustrate a method of using the packaging system of FIG. 2 to secure the IUD of FIG. 1 to the insertion tube of FIG. 2.

Referring to FIG. 8, the user maintains a force against the arms 236, 238 (e.g., squeezes the arms 236, 238 together) until the arms 236, 238 are substantially parallel to the elongate body 220 such that the arms 106, 108 of the IUD 100 are collapsed against the shaft 104 of the IUD 100. For example, when the channels 244, 246 of the arms 236, 238 are positioned substantially parallel to the elongate body 220, the arms 106, 108 of the IUD 100 are folded against and substantially parallel to the shaft 104 of the IUD 100.

Figure 9:
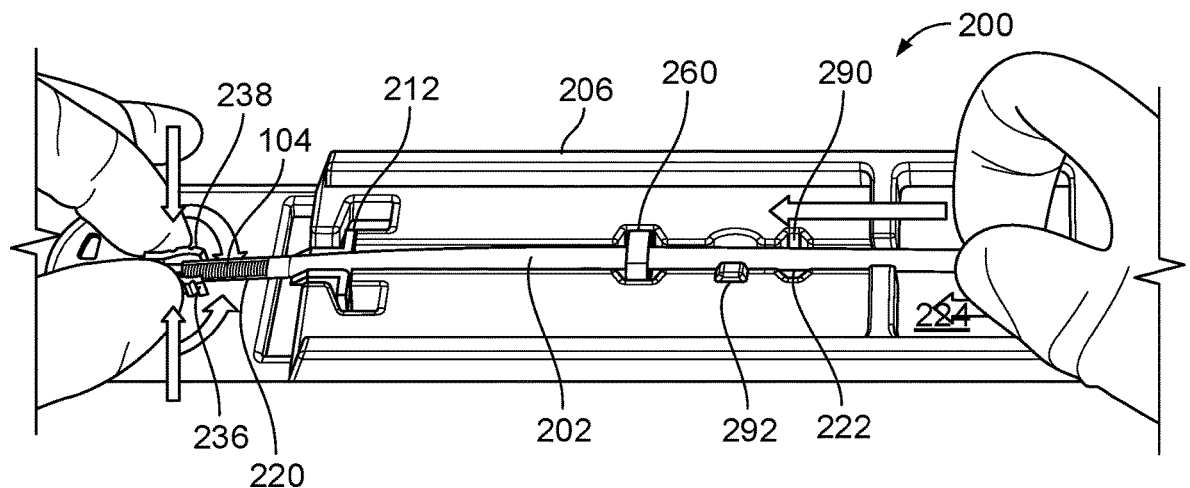

Referring to FIG. 9, once the arms 106, 108 of the IUD 100 are folded against the shaft 104 of the IUD 100, the insertion tube 202 is moved distally along the slot 222 of the tray 206 and the channel 252 of the receptacle 212 towards the IUD 100. For example, the user can grasp a portion of the insertion tube 202 positioned within the recessed gripping region 224 of the tray 206 and slide the insertion tube 202 distally towards the loading device 204 while maintaining the arms 236, 238 parallel to the elongate body 220. The insertion tube 202 is slid distally until the distal end of the insertion tube 202 slides over proximal ends of the folded arms 106, 108 that extend past ends of the channels 244, 246 of the arms 236, 238 of the loading device 204.

Figure 10:
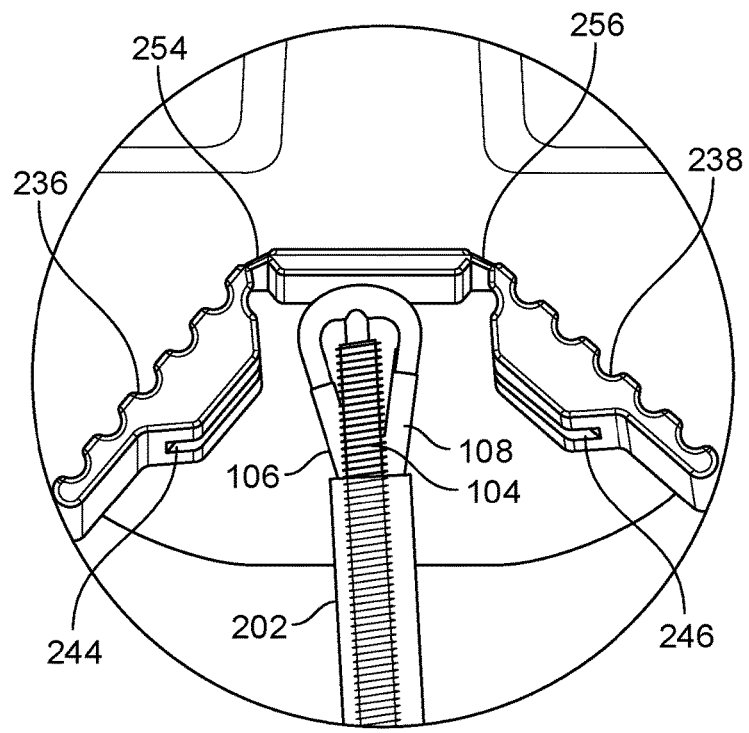

Referring to FIG. 10, sliding the insertion tube 202 over the arms 106, 108 of the IUD 100 captures and maintains the arms 106, 108 in the folded positions against the shaft 104. Once the insertion tube 202 has been positioned over the arms 106, 108, the user can release the arms 236, 238 of the loading device 204 from his or her fingers to allow the arms 236, 238 to flexibly pivot away from the IUD 100. If one or both of the arms 106, 108 of the IUD 100 are not appropriately positioned within the insertion tube 202 at this point, then the user can slide the insertion tube 202 proximally back towards an initial position, and the process described with respect to FIGS. 7-10 can be repeated until the proximal ends of the arms 106, 108 of the IUD are securely positioned within the insertion tube 202.

Figure 11:
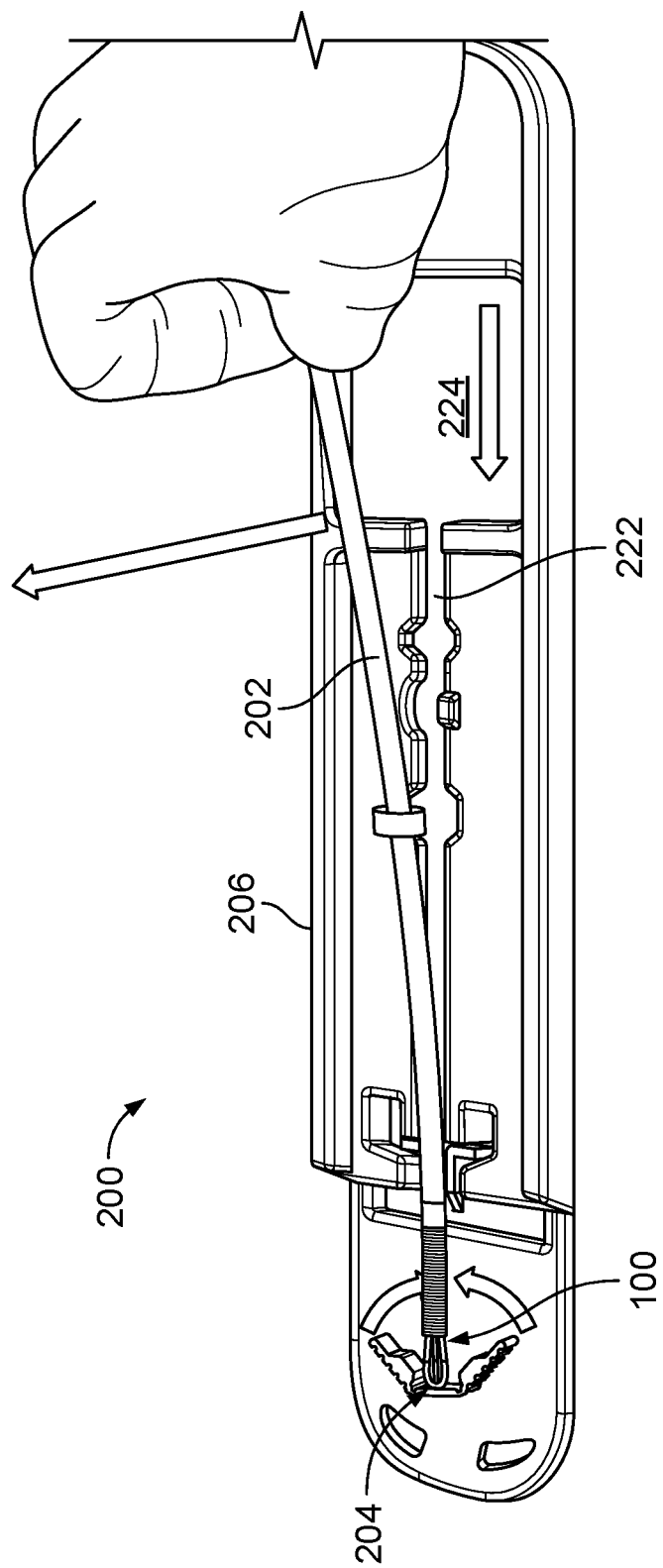

Referring to FIG. 11, once the arms 106, 108 of the IUD 100 are secured within the insertion tube 202, the insertion tube 202, carrying the IUD 100, is removed from sequentially from the tray 206 and from the loading device 204. For example, the user can grasp a portion of the insertion tube 202 positioned in the gripping region 224 with his or her fingers and lift the insertion tube 202 out of the slot 222 in the tray 206 and out of the receptacle 212 of the loading device 204. Since the arms 106, 108 of the IUD 100 are secured to the insertion tube 202, the IUD 100 is also removed along with the insertion tube 202.

Figure 12:
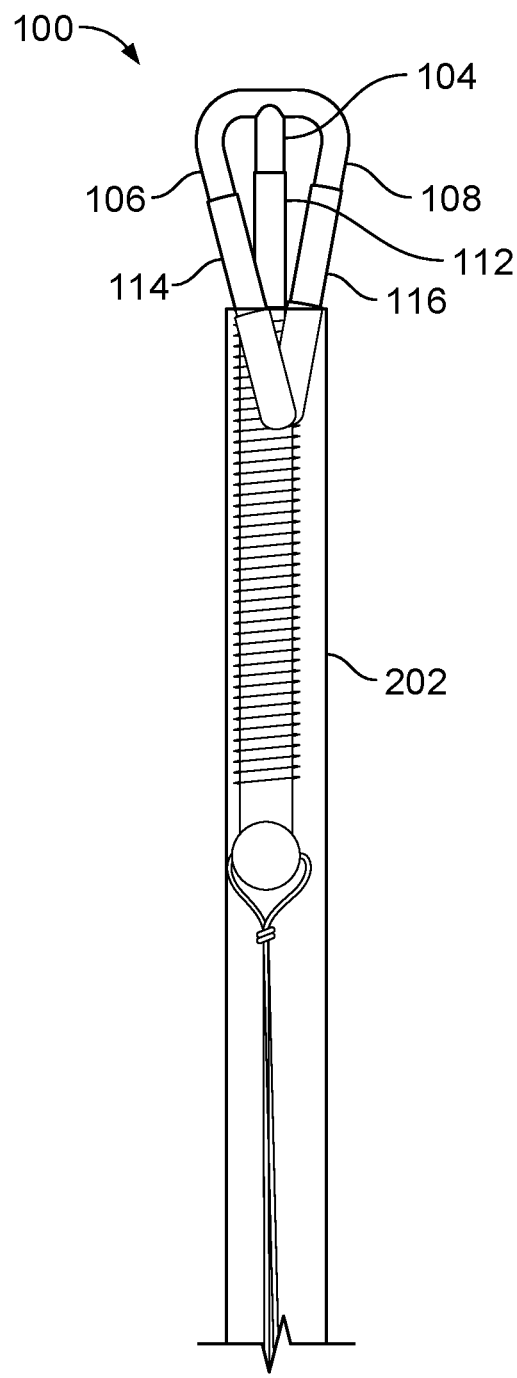
FIG. 12 is a perspective view of the IUD of FIG. 1 secured to the insertion tube of FIG. 2 in a folded configuration.

Referring to FIG. 12, the IUD 100 is now prepared for implantation (e.g., deployment) within the patient. As depicted, the arms 106, 108 of the prepared IUD 100 are folded against the shaft 104 of the IUD 100, and a portion of each of the arms 106, 108 of the IUD 100 is contained within the insertion tube 202. Furthermore, a portion of the shaft 104 of the IUD 100 is also captured within the insertion tube 202.

Figure 13:
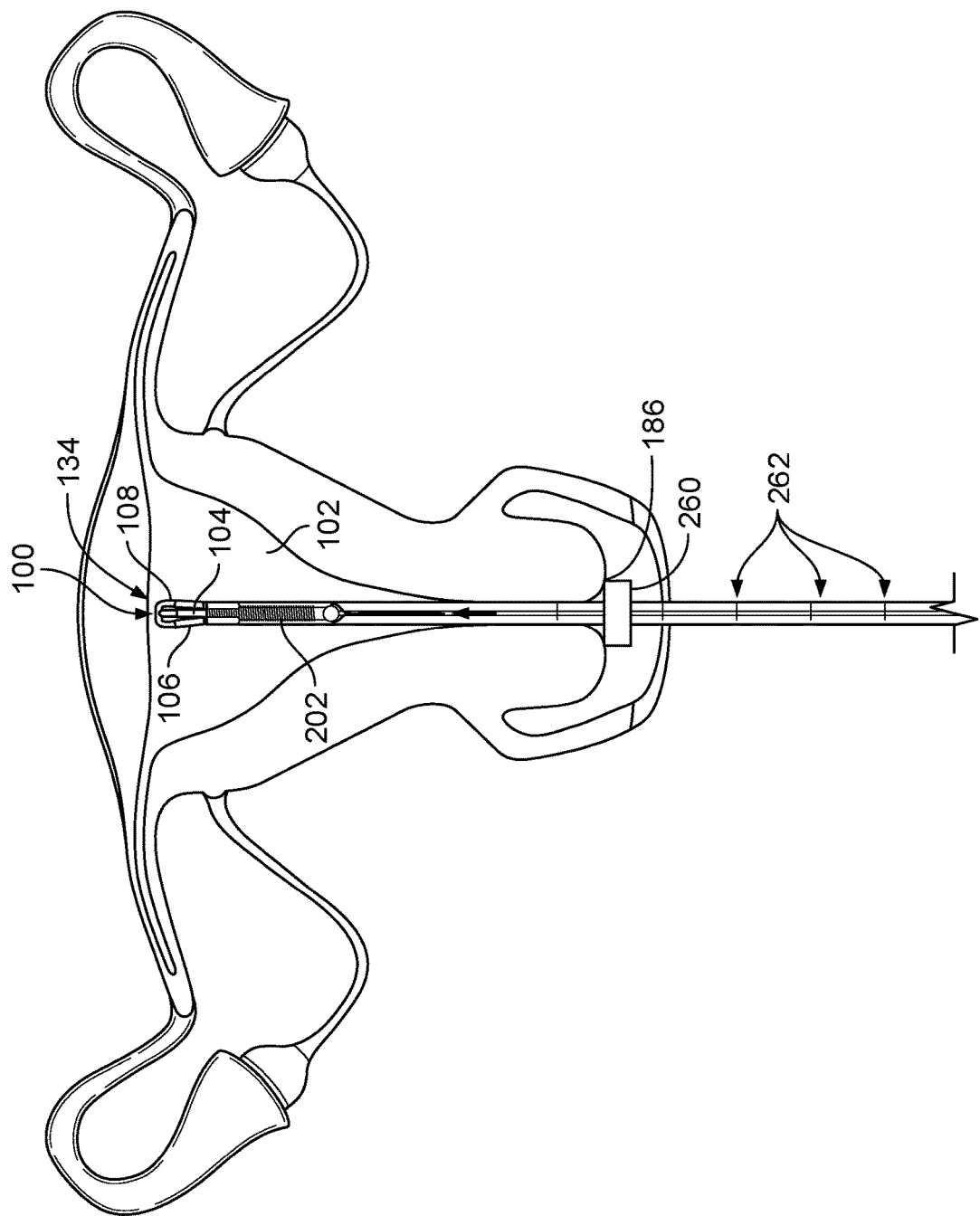
FIGS. 13-15 illustrate a method of implanting the IUD of FIG. 1 into the uterus of a patient using the insertion tube of FIG. 2.
Figure 14:
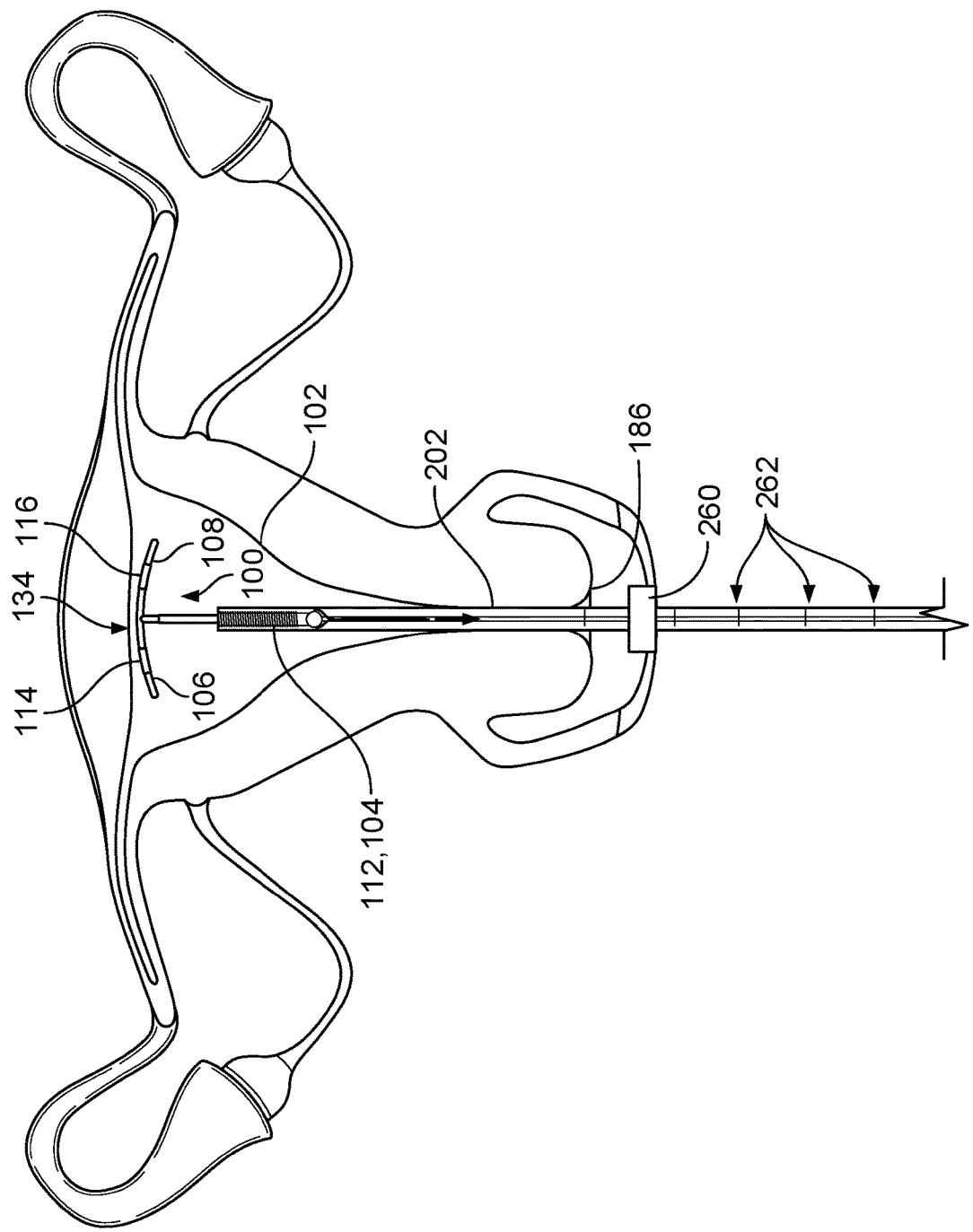
Figure 15:
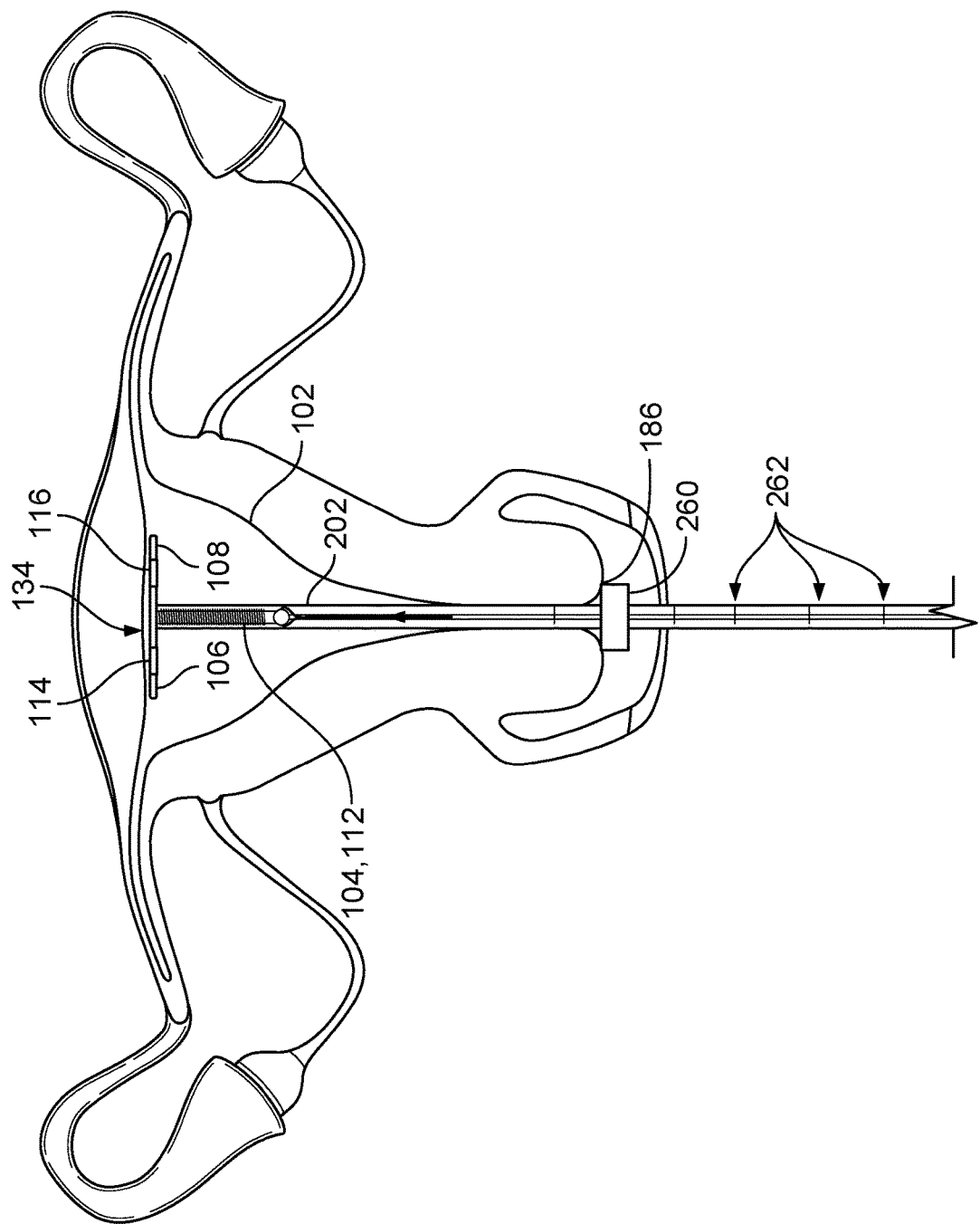

FIGS. 13-15 illustrate a method of implanting the IUD 100 into the uterus 102 of the patient using the insertion tube 202 and the rod 235 (e.g., positioned within the insertion tube 202). Prior to inserting the IUD 100 into the uterus 102, the depth of the uterus 102 (e.g., of the uterine cavity) is measured by inserting a sterile uterine sound into the uterus 102. The measurement indicator 260 is moved along the insertion tube 202 to be aligned with a ruler marking 262 on the insertion tube 202 that corresponds to the depth measurement determined using the uterine sound. When the IUD 100 is properly positioned at the fundus 134 of the uterus 102, the measurement indicator 260 is positioned against (e.g., abuts) the cervix 186 of the patient, as depicted in FIG. 13. In this manner, the measurement indicator 260 ensures proper positioning of the insertion tube 202 and the IUD 100 within the uterus 102. Once the measurement indicator 260 is aligned with the proper ruler marking 262, the rod 235 (e.g., already positioned within the insertion tube 202) is adjusted to contact the proximal end of the shaft 104 of the IUD 100.

Referring to FIG. 13, the insertion tube 202, carrying the IUD 100, is passed through the cervical canal into the uterus 102 until the IUD 100 touches the fundus 134 of the uterus. When the distal end of the IUD 100 is properly positioned against the fundus 134 of the uterus 102, the measurement indicator 260 abuts the cervix 186 of the patient, as depicted in FIG. 13.

Referring to FIG. 14, once the insertion tube 202 is positioned in the cervical canal such that the exposed end of the IUD 100 is touching the fundus 134 of the uterus, the insertion tube 202 is pulled proximally away from the IUD 100 until the arms 106, 108 of the IUD 100 are released from the insertion tube 202. The rod 235 inside of the insertion tube 202 is held steady while the insertion tube 202 is pulled proximally to release the arms 106, 108 of the IUD 100. For example, the insertion tube 202 may be pulled proximally until the proximal end of the insertion tube 202 contacts the end portion 232 (shown in FIG. 2) of the rod 235. In some examples, the insertion tube 202 is pulled proximally by a distance of about 0.4 cm to about 0.6 cm (e.g., about 0.5 cm) to release the arms 106, 108 of the IUD 100.

Referring to FIG. 15, once the arms 106, 108 of the IUD 100 are released from the insertion tube 202, the insertion tube 202 is moved distally further into the uterus 102 to push the IUD 100 towards the fundus 134 to ensure that the arms 106, 108 of the IUD 100 are placed at the deepest position in the uterus 102 (e.g., against the fundus 134 of the uterus 102).

After ensuring proper placement of the IUD 100 in the uterus 102, the rod (235 and the insertion tube 202 are removed from the cervical canal of the patient. In some examples, the rod 235 is first removed from the patient while the insertion tube 202 is held steady, and the insertion tube 202 is then removed after removing the rod 235. In some examples, after removal of the insertion tube 202 from the patient, the one or more threads 110 (shown in FIG. 1) coupled to the shaft 104 are trimmed. In some implementations, the threads of the IUD 100 are trimmed so that a length of about 1.5 cm to about 2.0 cm (e.g., about 2.0 cm) of the one or more threads extend out the cervical canal and into the vagina of the patient.

Figure 16:
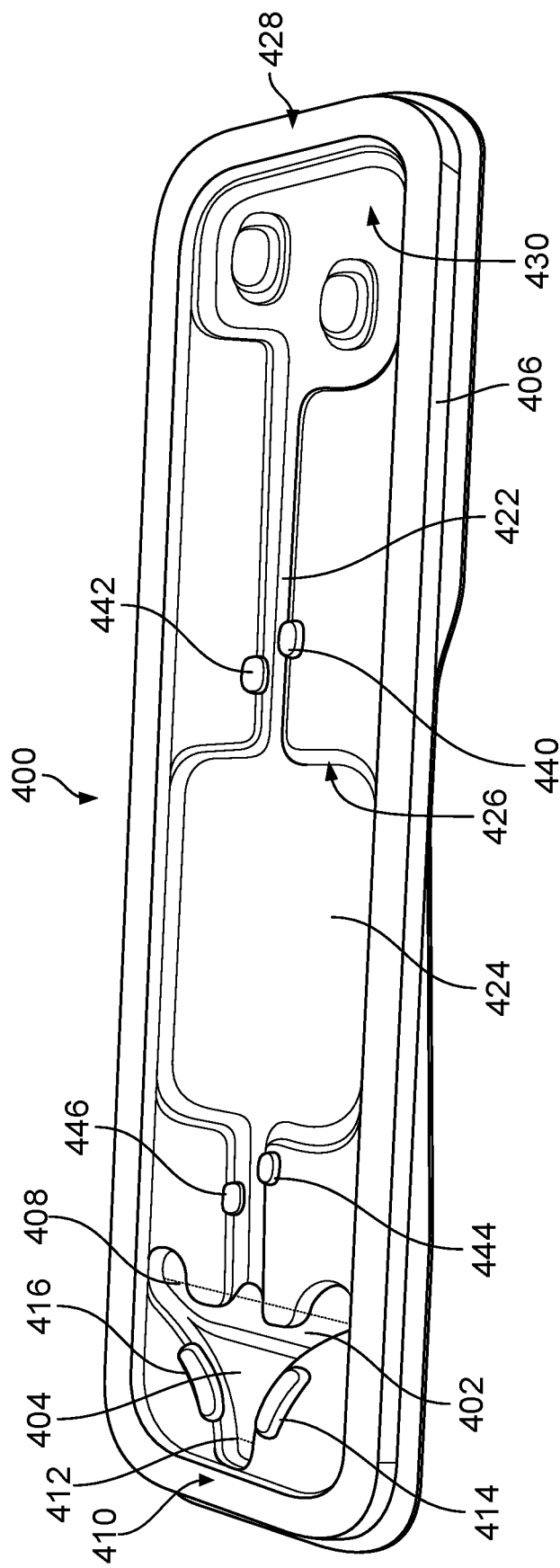
FIG. 16 is a perspective view of a portion of a packaging system for securing the IUD of FIG. 1 to the insertion tube of FIG. 2.
Figure 17:
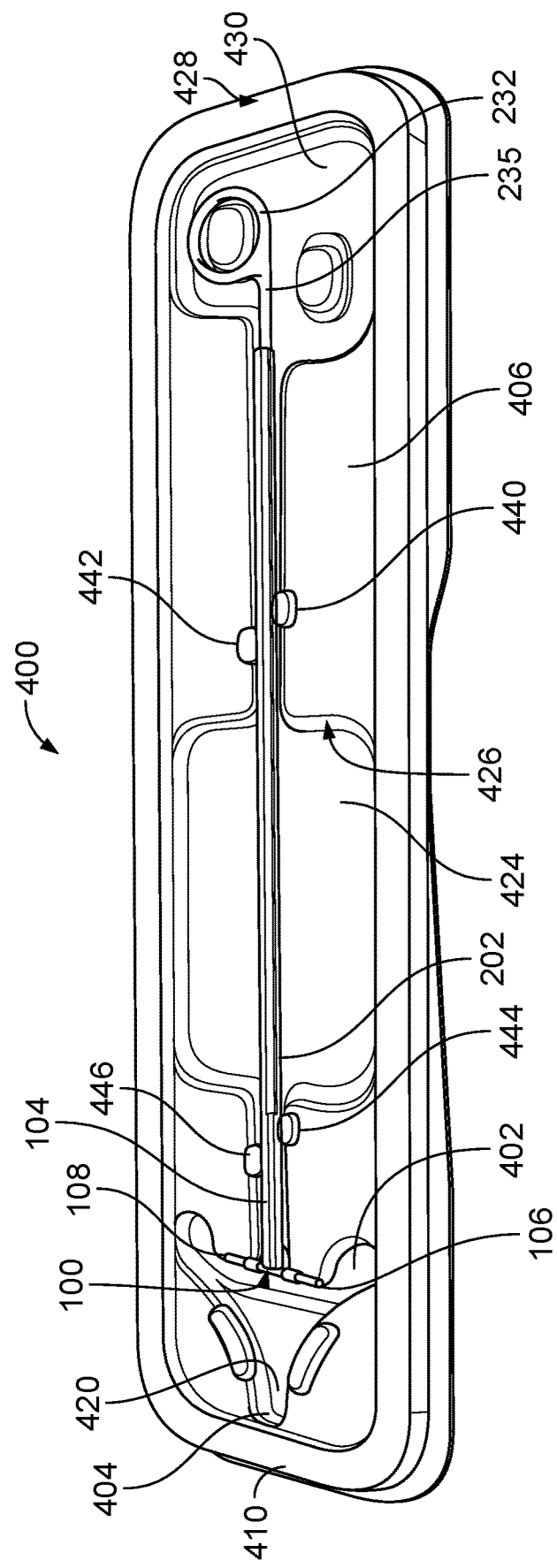
FIGS. 17-20 illustrate a method of securing the IUD of FIG. 1 to the insertion tube of FIG. 2 using the packaging system of FIG. 16.

While certain embodiments have been described above, other embodiments are possible. For example, while the packaging system 200 for securing an intrauterine device 100 to an insertion tube 202 has been described and illustrated as including a loading device 204 with pivotable arms 236, 238, in some embodiments, a system that is similar in function to the system 200 includes a one or more receptacles sized to fold the arms 106, 108 of an IUD 100 rather than a loading device 204 with pivotable arms 236, 238. Referring to FIGS. 16 and 17, a packaging system 400 that houses an IUD 100 is designed for securing the IUD 100 to an insertion tube 202. The packaging system 400 includes a tray 406 defining multiple depressions, including a slot 422, a first receptacle 402, a second receptacle 404, a gripping region 424, and a proximal depression 430. In some examples, the tray 406 has a length of about 28.3 cm to about 29.9 cm (e.g., about 29.1 cm), a width of about 22.6 cm to about 24.2 cm (e.g., about 23.4 cm), and a height of about 0.9 cm to about 1.1 cm (e.g., about 0.98 cm).

As depicted in FIG. 16, the slot 422 extends along the length of the tray 406. The slot 422 accommodates an insertion tube 202 and restricts lateral movement and angular movement of the insertion tube 202 outside the slot 422. In some examples, the slot 422 has a length of about 2.9 cm to about 3.4 cm (e.g., about 3.15 cm), a width of about 0.48 cm to about 0.53 cm (e.g., about 0.51 cm), and a depth of about 0.63 cm to about 0.68 cm (e.g., about 0.66 cm).

The tray 406 also include flanges 440, 442, 444, 446 positioned adjacent to the slot 422 along the length of the slot 422. The flanges 440, 442, 444, 446 narrow an axial opening of the slot 422 to help retain the insertion tube 202 in the slot 422 and prevent dislodgement of the insertion tube 202 from the tray 406 during transit of the system 400 prior to preparation of the IUD 100 for implantation. The insertion tube 202 can be detached from the tray 406 without damaging the insertion tube 202 or the tray 406.

The tray 406 defines a first receptacle 402 located adjacent the distal end of the slot 422. The first receptacle 402 accommodates the arms 106, 108 of the IUD 100 in an initial configuration (e.g., a packaged state) in which the arms 106, 108 are substantially perpendicular to the shaft 104 of the IUD 100, as depicted in FIG. 17. For example, a width 408 of the first receptacle 402 is larger than the distance between the end of the first arm 106 and the end of the second arm 108 when the arms 106, 108 are substantially perpendicular to the shaft 104 of the IUD 100. In some examples, the first receptacle 402 has a width of about 4.4 cm to about 4.6 cm (e.g., about 4.50 cm), a length of about 1.4 cm to about 1.6 cm (e.g., about 1.50 cm), and a depth of about 7.8 cm to about 7.9 cm (e.g., about 7.85 cm).

Figure 19:
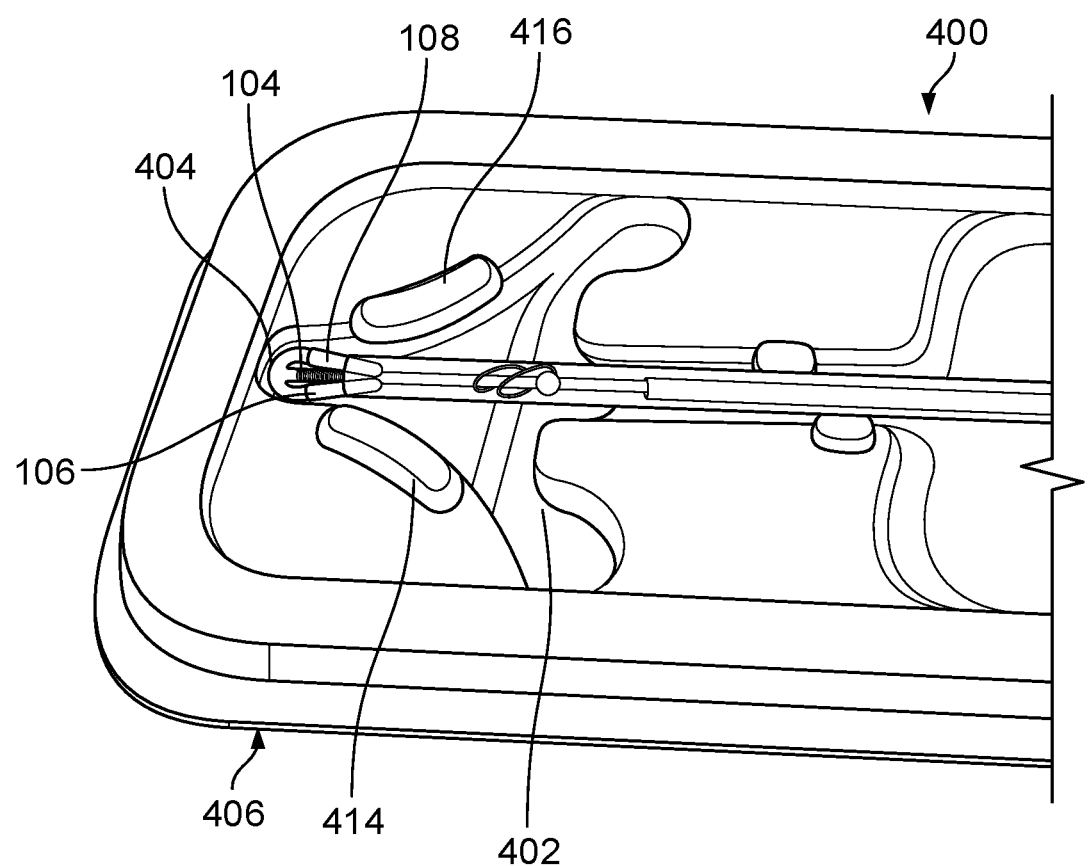

Referring to FIGS. 16 and 17, the second receptacle 404 is located adjacent to the first receptacle 402 and to the distal end 410 of the tray 406. The second receptacle 404 has a minimum width 412 sized to receive the arms 106, 108 of the IUD 100 in a collapsed or folded state (as depicted in FIG. 19). For example, the second receptacle 404 is formed as a generally triangular-shaped depression that narrows to the width 412 near the distal end 410 of tray 406. The shape of second receptacle 404 causes the arms 106, 108 of the IUD 100 to be pushed inwards towards the shaft 104 of the IUD 100 through contact with tapered walls 414, 416 of the second receptacle 404 as the IUD 100 is pushed distally through the second receptacle 404. The second receptacle 404 also defines a floor 420 that supports the IUD 100 as the IUD is moved distally along the second receptacle 404.

The gripping region 424 provides space for a user to grasp a portion of the insertion tube 202 positioned within the gripping region 424 with his or her fingers and slide the insertion tube 202 distally along the slot 422 to capture the folded arms 106, 108 of the IUD 100 within the insertion tube 202. In some examples, the gripping region 424 defined within the tray 406 has a length of about 4.2 cm to about 4.4 cm (e.g., about 4.31 cm), a width of about 3.9 cm to about 4.1 cm (e.g., about 4.0 cm), and a depth of about 0.9 cm to about 1.0 cm (e.g., about 0.95 cm). In some examples, a proximal end 426 of the gripping region 224 is positioned about 12.6 cm to about 12.8 cm (e.g., about 12.7 cm) apart from a proximal end 428 of the tray 406.

The tray 406 further defines a proximal depression 430 located near the proximal end 428 of the tray 406. The proximal depression 430 accommodates the end portion 232 of a rod 235 used to push the IUD 100 positioned in the first receptacle 402 through the second receptacle 404. In some examples, the proximal depression 430 defined within the tray 406 has a length of about 4.8 cm to about 5.0 cm (e.g., about 4.9 cm) and a depth of about 0.9 cm to about 1.0 cm (e.g., about 0.95 cm). In some examples, the width of the depression forming the proximal depression 430 is about 3.9 cm to about 4.1 cm (e.g., about 4.0 cm).

Figure 18:
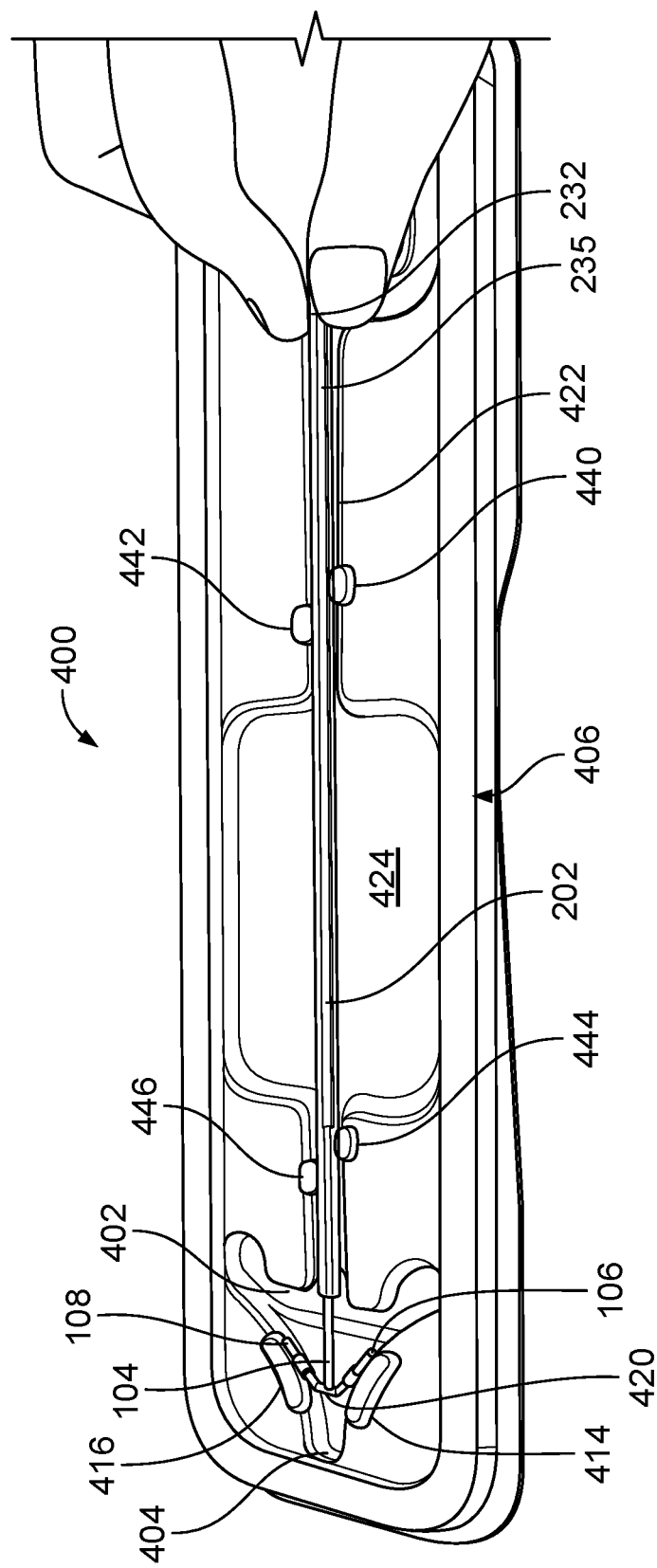

FIGS. 17-19 illustrate a method of securing the IUD 100 to the insertion tube 202 using the packaging system 400. Referring to FIG. 17, the arms 106, 108 of the IUD 100 are substantially perpendicular to the shaft 104 of the IUD 100 and are positioned within the first receptacle 402, with the arms 106, 108 spanning the width 408 of the first receptacle 402, as discussed above. The rod 235 is positioned within the insertion tube 202 and circular end portion 232 (e.g., a ring) is positioned within the proximal depression 430 to prevent movement of the rod 235. The insertion tube 202 is positioned within the slot 422 and is releasable coupled to the tray 406 by flanges 440, 442, 444, 446.

Referring to FIG. 18, the end portion 232 of the rod 235 is rotated upwards to lift the end portion 232 out of the proximal depression 430 so that the rod 235 can be advanced distally through the insertion tube 202 towards the IUD 100 to apply a force to the end of the shaft 104 to move the arms 106, 108 from the first receptacle 402 into the second receptacle 404. For example, the user can grasp the end portion 232 and push the rod 235 through the insertion tube 202 to push the arms 106, 108 of the IUD 100 distally into the second receptacle 404. As the rod 235 pushes the arms 106, 108 into the second receptacle 404 along the floor 420, the arms 106, 108 are pressed against the walls 414, 416, therefore causing the arms 106, 108 to fold inwards towards the shaft 104.

Referring to FIG. 19, the arms 106, 108 are pushed into a distal end of the second receptacle 404 to complete the folding of the arms 106, 108 into a collapsed state against the shaft 104 of the IUD 100. Once the arms 106, 108 are folded against the shaft 104, the insertion tube 202 is slid distally along the slot 422 and over proximal ends of the folded arms 106, 108, as depicted in FIG. 19.

Figure 20:
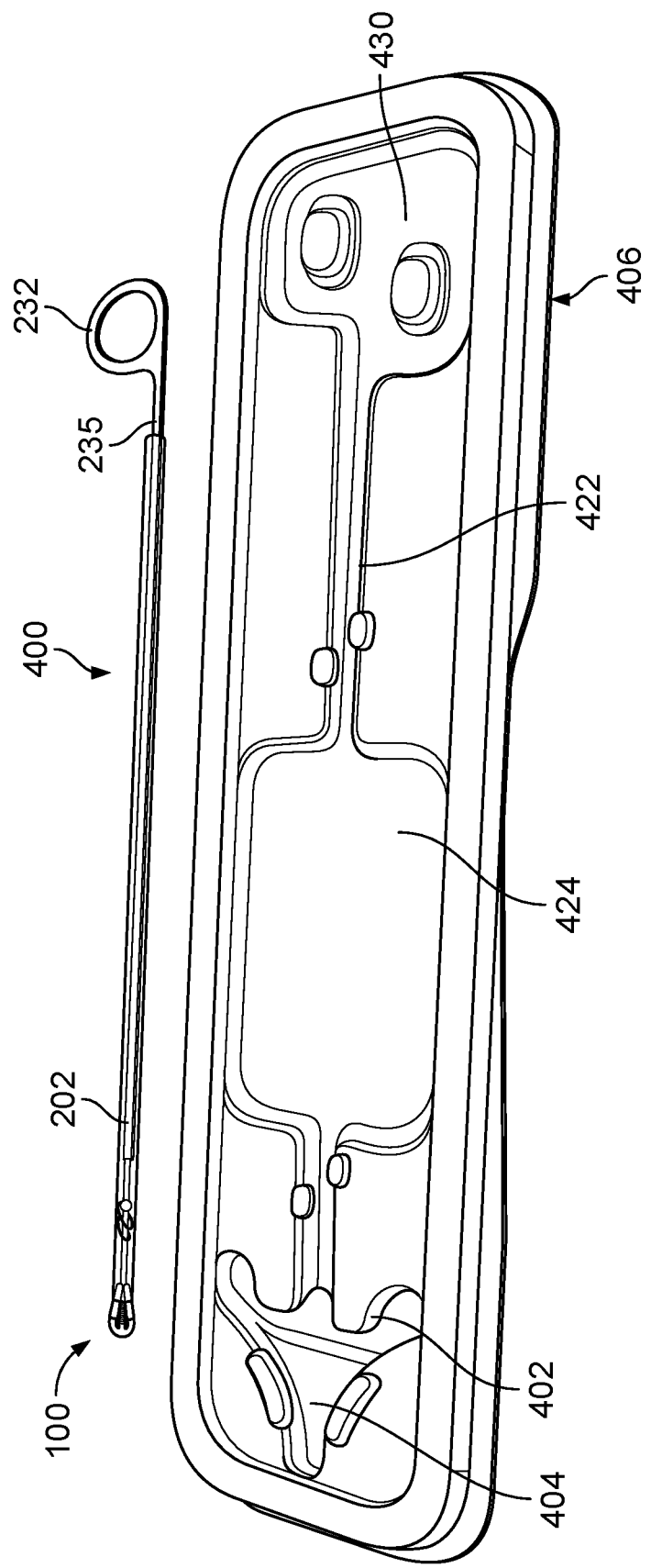

Referring to FIG. 20, once the insertion tube 202 is positioned over the folded arms 106, 108 to maintain the collapsed state of the arms 106, 108, the IUD 100, the insertion tube 202, and the rod 235 can be removed from the tray 406 by lifting up on the insertion tube 202, and the IUD 100 is ready for implantation in the uterus 102 of a patient.

The packaging system 200 has been described and illustrated with respect to a user pivoting the arms 236, 238 of the loading device 204 to fold the arms 106, 108 of the IUD 100 and sliding the insertion tube 202 over the folded arms 106, 108. However, in some embodiments, a packaging system that is otherwise similar in construction and function to the packaging system 200 includes a loading device with a string that is used to pivot arms of the loading device to fold the arms 106, 108 of the IUD 100 and to secure the folded arms 106, 108 into an insertion tube 202.

Figure 21:
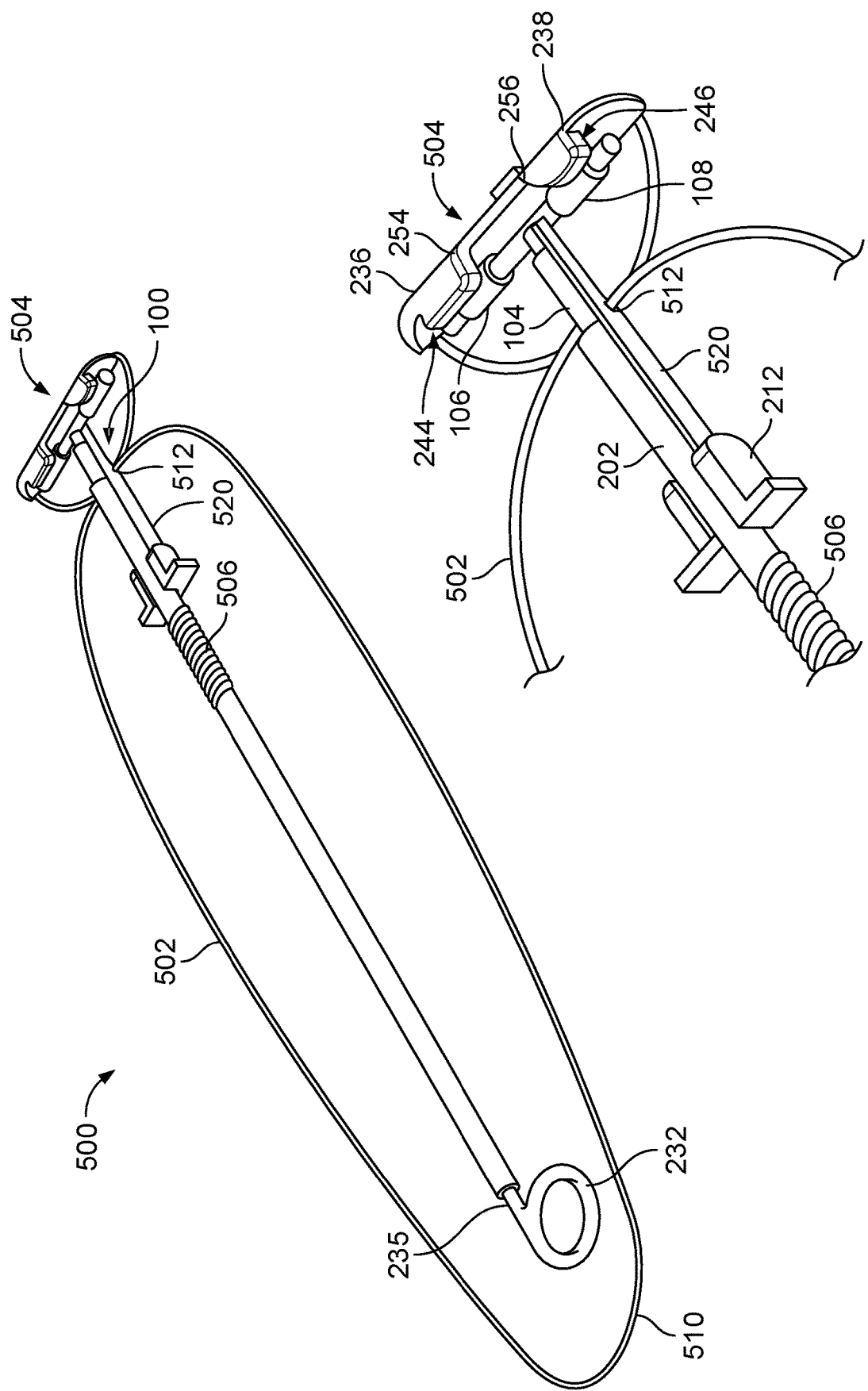
FIG. 21 is a perspective view of a portion of a packaging system that houses the IUD of FIG. 1 along with the insertion tube of FIG. 2.

For example, as shown in FIG. 21, such a packaging system 500 is designed to house an IUD 100 along with an insertion tube 202 and a rod 235. The packaging system 500 includes a tray (not shown) that is similar in structure and function to the tray 206, a lid (not shown) that covers the tray, and a loading device 504. The loading device 504 is substantially similar in construction and function to the loading device 204, except that the loading device 504 further includes a string 502 (e.g., a suture, a wire, or another type of string) and an elongate body 520 that defines an opening 512 for allowing passage of the string 502. Accordingly, in addition to the elongate body 520, the loading device 504 further includes the arms 236, 238 and the receptacle 212.

The string 502 is attached to the arms 236, 238 in a manner such that movement of the string 502 applies a force to the ends of the arms 236, 238. For example, the string 502 may be secured to a top surface of the arms 236, 238 and pass over the ends the arms 236, 238, or the string 502 may terminate at the ends of the arms 236, 238. The string 502 also crosses over itself and passes through the opening 512 in the elongate body 220 to form a closed loop.

The packaging system 500 further includes a spring 506 that is positioned parallel to the insertion tube 202 and that is retained by the tray. A distal end of the spring 506 abuts the receptacle 212, thereby applying a distally directed force to the loading device 504 that maintains the loading device 504 in place within the tray of the packaging system 500 while the string 502 is pulled by the user, as will be discussed in more detail below. Example materials from which the spring 506 can be made include steel, metal alloys, and plastic (e.g., polyetherimides (PEI) and thermoplastic elastomers (TPE)).

Figure 22:
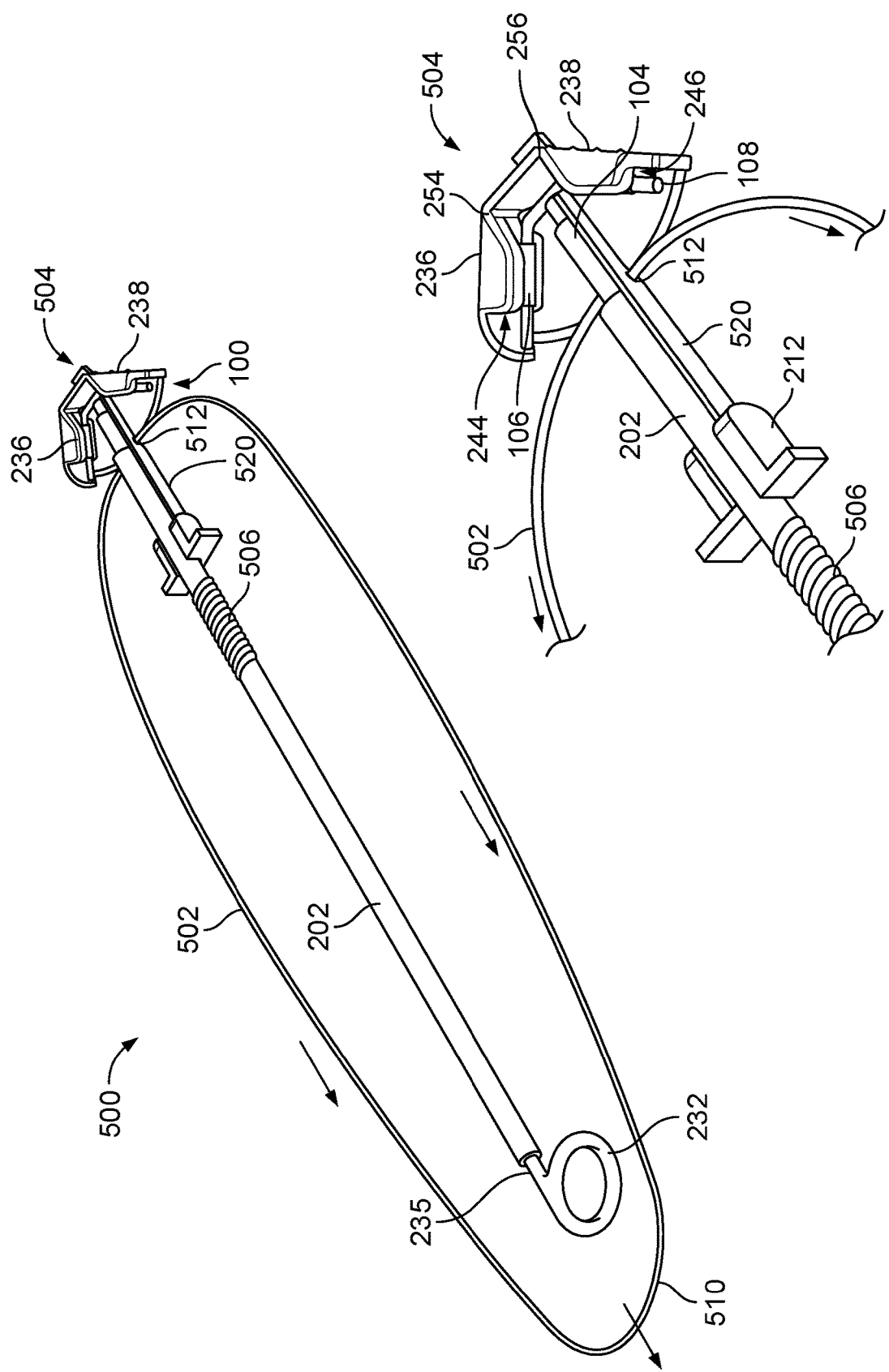
FIGS. 22-24 illustrate a method of securing the IUD of FIG. 1 to the insertion tube of FIG. 2 using the packaging system of FIG. 21.
Figure 23:
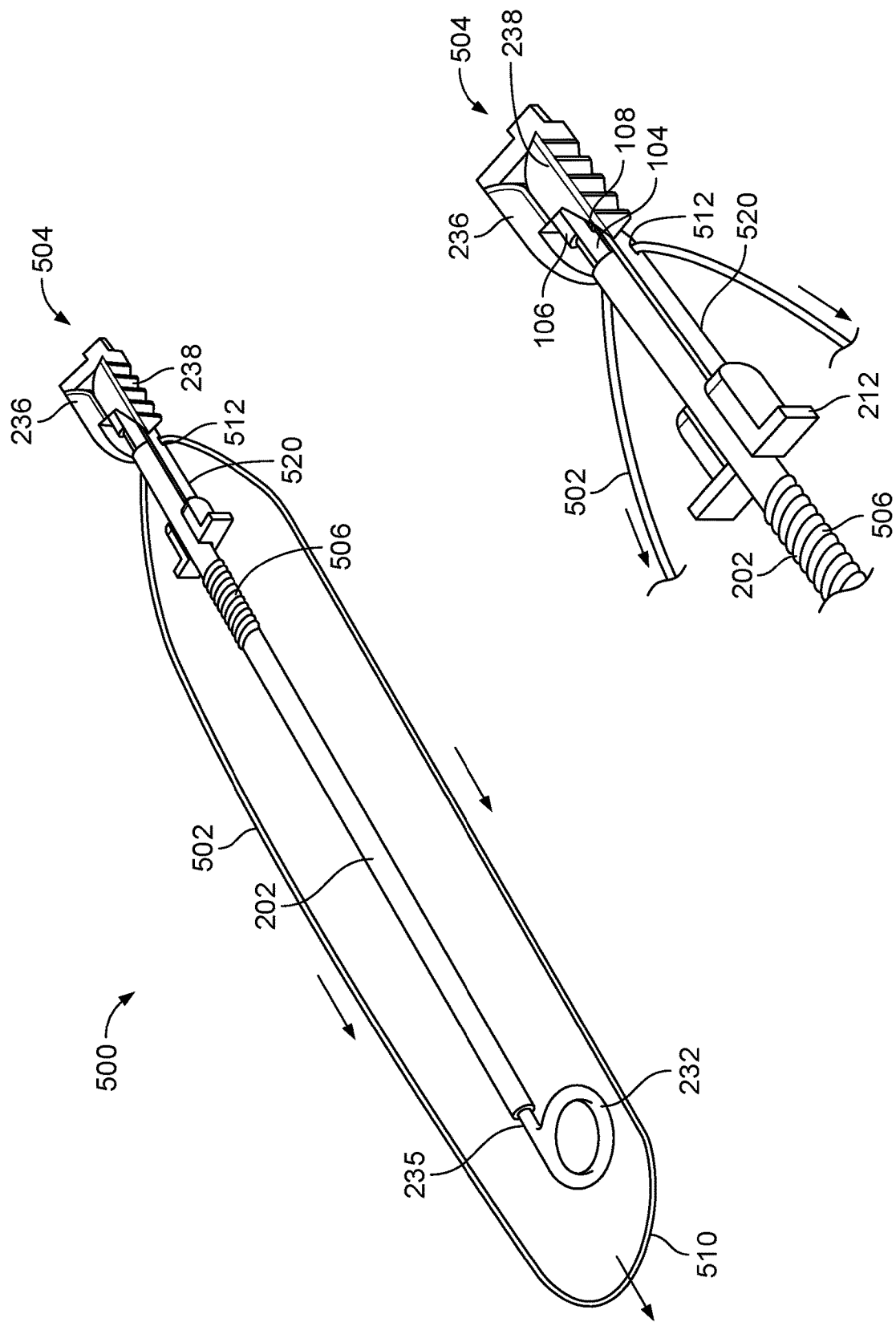
Figure 24:
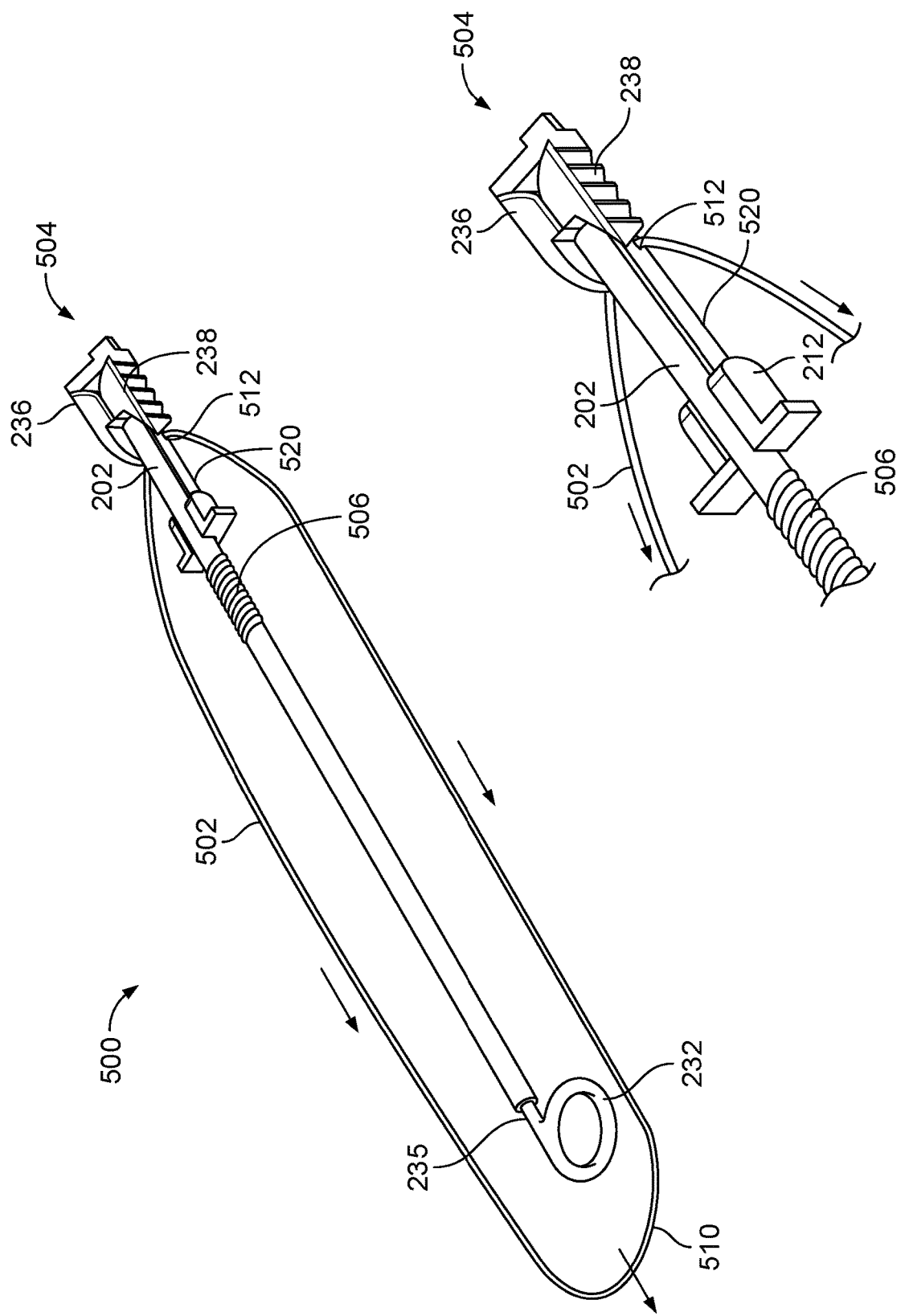

FIGS. 22-24 illustrate a method of securing the IUD 100 to the insertion tube 202 using the packaging system 500. Referring to FIG. 22, the arms 106, 108 of the IUD 100 are coupled to the channels 244, 246 of the arms 236, 238 of the loading device 504, and the insertion tube 202 is coupled to the receptacle 212 of the loading device 504. A user can pull proximally on a looped end 510 of the string 502 away from the loading device 504 to pivot the arms 236, 238 of the loading device 504 inward towards the elongate body 520, thereby also folding the arms 106, 108 of the IUD 100 inward towards the shaft 104 of the IUD 100.

Referring to FIG. 23, a proximally directed force is continually applied to the looped end 510 of string 502 until the arms 236, 238 are substantially parallel to the elongate body 520 of the loading device 504 and the arms 106, 108 of the IUD 100 are folded against the shaft 104 of the IUD 100 in a collapsed configuration.

Referring to FIG. 24, once the proximally directed force on the looped end 510 of the string 502 overcomes the distally directed force exerted by the spring 506 on the loading device 504, the loading device 504 moves proximally to compress the spring 506. The insertion tube 202 can be held in place by the user while the user continues to pull the string 502 such that the loading device 504 continues to move proximally, causing the ends of the folded arms 106, 108 to be drawn into the insertion tube 202 to secure the IUD 100 to the insertion tube 202.

Once the folded arms 106, 108 are positioned within the insertion tube 202, the user can release the string 502 to allow the arms 236, 238 to pivot back towards the initial configuration, thereby releasing the IUD 100 from the loading device 504. The insertion tube 202 can then be lifted up from the tray. At this point, the IUD 100, secured to the insertion tube 202, is ready for placement in the uterus of a patient.

Figure 25:
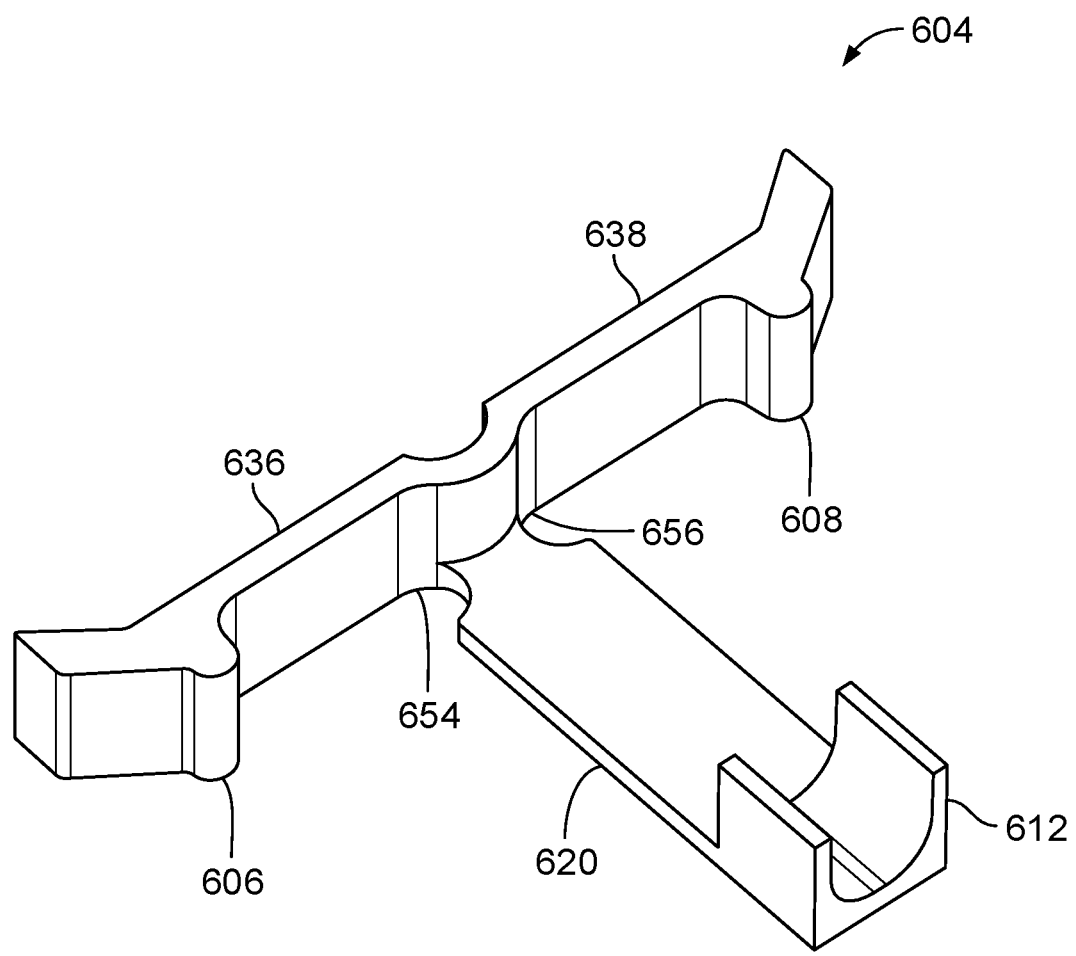
FIG. 25 is a perspective view of a loading device for securing the IUD of FIG. 1 to the insertion tube of FIG. 2.

While the loading devices 204, 504 have been described and illustrated as including arms 236, 238 that form channels 244, 246 for receiving arms 106, 108 of an IUD 100, in some embodiments, a loading device that is similar in construction and function to the loading devices 204, 504 can be formed without such channels. For example, FIG. 25 illustrates such as loading device 604. The loading device 604 includes an elongate body 620, a receptacle 612, and a pair of arms 636, 638.

The receptacle 612 is sized and shaped to receive an insertion tube 202 and to restrict lateral movement of the insertion tube 202.

The arms 636, 638 respectively extend from the elongate body 620 at flexible locations 654, 656. The flexible locations 654, 656 are substantially similar in construction and function to the flexible locations 654, 656 such that arms 636, 638 are pivotable inward towards the elongate body 620 about the flexible locations 654, 656, as described and illustrated with respect to the loading devices 204, 504.

Each of the arms 636, 638 includes a flange 606, 608 positioned to engage with the end of a respective arm 106, 108 of the IUD 100 when the IUD 100 is positioned within the loading device 604. For example, the distance between each of the flanges 606, 608 is less than the distance between the ends of the arms 106, 108 of the IUD 100 when the arms 106, 108 are substantially perpendicular to the shaft 104 of the IUD 100. As such, when the arms 636, 638 are pivoted inward, the flanges 606, 608 push the arms 106, 108 of the IUD 100 inward to fold the arms 106, 108 toward the shaft 104.

Figure 26:
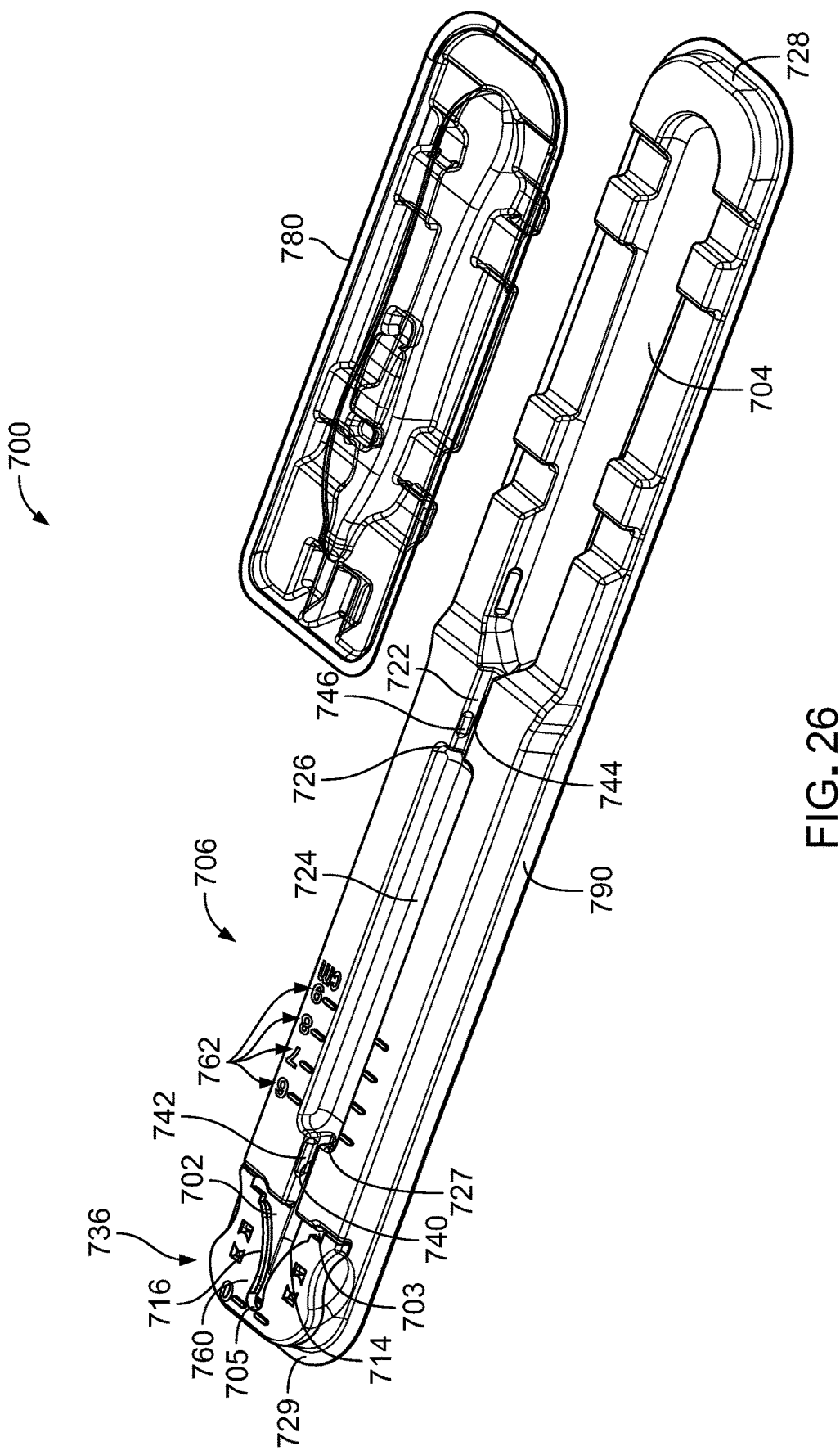
FIG. 26 is a perspective view of a packaging system for securing the IUD of FIG. 1 to the insertion tube of FIG. 2.
Figure 27:
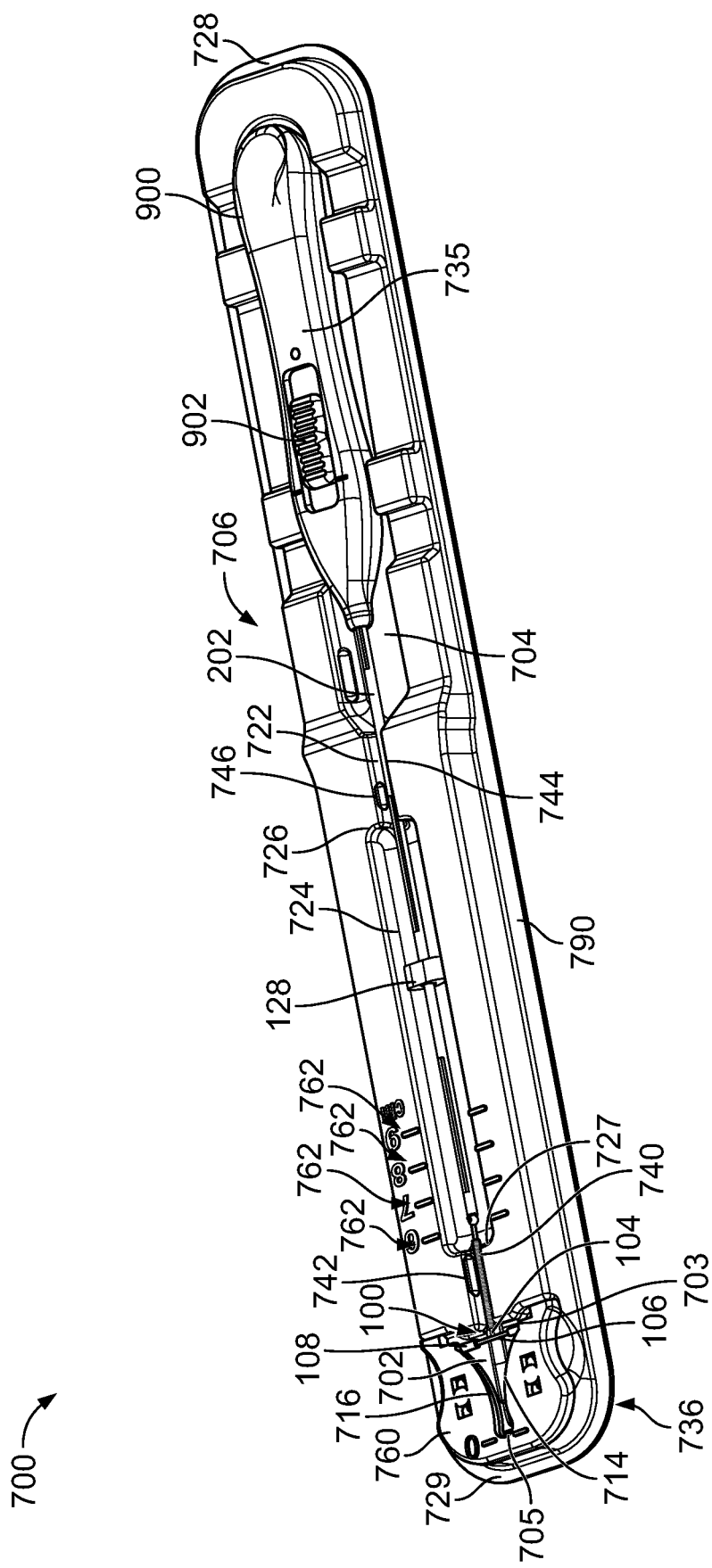
FIGS. 27-29 illustrate a method of securing the IUD of FIG. 1 to the insertion tube of FIG. 2 using the packaging system of FIG. 26.

FIGS. 26 and 27 depict another example packaging system 700 that includes one or more receptacles formed to facilitate folding of the arms 106, 108 of an IUD 100 rather than a loading device 204 with pivotable arms 236, 238. For example, the packaging system 700 houses the IUD 100 and is designed for securing the IUD 100 to an insertion tube 202. The packaging system 700 includes a tray 706 defining multiple depressions formed in either of a main body 790 of the tray 706 or a loading aid 760 of the tray. In some embodiments, the main body 790 and the loading aid 760 are formed as two separate components that are assembled together during manufacture. In other embodiments, the tray 706 is provided as a single, unitary component that integrally defines the main body 790 and the loading aid 760. The depressions include a distal depression 702, a proximal depression 704, and a slot 722 connecting the distal depression 702 and the proximal depression 704. As depicted in FIG. 27, the slot 722 accommodates an insertion tube 202 and restricts lateral movement and angular movement of the insertion tube 202 outside the slot 722.

As depicted in FIGS. 26 and 27, the slot 722 can include a gripping region 724 that is wider than the rest of the slot 722. The gripping region 724 provides space for a user to grasp a cervical collar 128 that is slidably coupled to the insertion tube 202 and positioned within the gripping region 724 when the insertion tube 202 is positioned within the slot 722. For example, when the insertion tube 202 is positioned in the slot 722, a user can grasp the cervical collar 128 positioned in the gripping region 724 with his or her fingers and slide the cervical collar 128 proximally or distally relative to the insertion tube 202 until the cervical collar 128 corresponds to a depth measurement determined using a uterine sound.

For example, as can be seen in FIGS. 26 and 27, the tray 706 can also include markings 762 indicating positions to place the cervical collar 128 for corresponding to the depth measurement. For example, if a patient has a measured uterine depth of 8 cm, a user can grasp the cervical collar 128 positioned in the gripping region 724 of the slot 722 with his or her fingers and slide the cervical collar 128 proximally or distally relative to the insertion tube 202 until the cervical collar 128 is aligned with the 8 cm marking 762 on the tray 706.

The tray 706 also includes flanges 740, 742, 744, 746 positioned adjacent the slot 722 along the length of the slot 722. The flanges 740, 742, 744, 746 narrow an axial opening of the slot 722 to help retain the insertion tube 202 in the slot 722 and prevent dislodgement of the insertion tube 202 from the tray 706 during transit of the system 700 prior to preparation of the IUD 100 for implantation. The insertion tube 202 can be detached from the tray 706 without damaging the insertion tube 202 or the tray 706.

Figure 30:
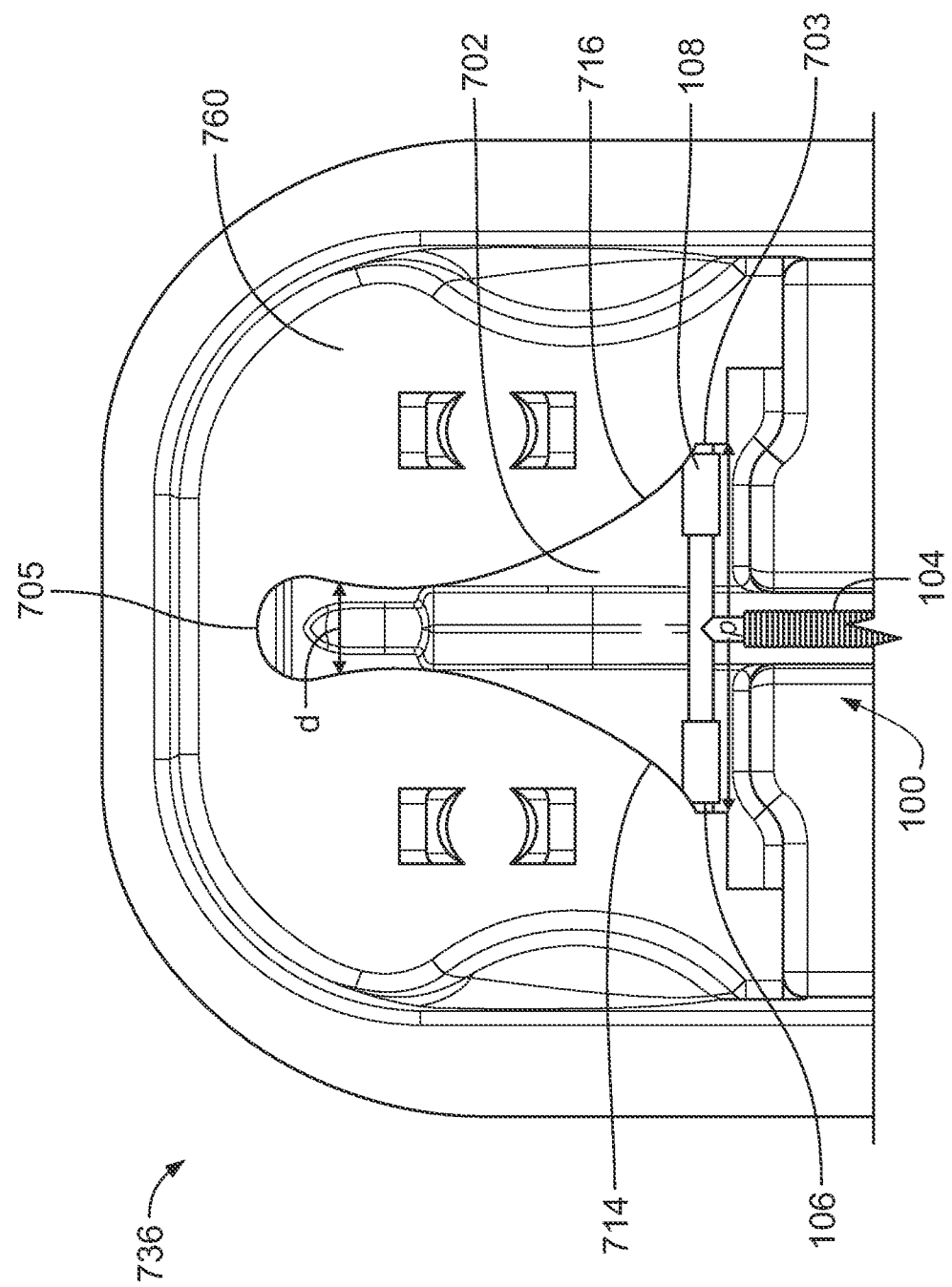
FIG. 30 is a top view of the distal portion of the packaging system of FIG. 26.

As depicted in FIGS. 26 and 27, the loading aid 760 is coupled to the distal portion 736 of the main body 790 of tray 706. The loading aid 760 defines the distal depression 702 located adjacent the distal end of the slot 722. The proximal end 703 of the distal depression 702 accommodates the arms 106, 108 of the IUD 100 in an initial configuration (e.g., a packaged state) in which the arms 106, 108 are substantially perpendicular to the shaft 104 of the IUD 100, as depicted in FIG. 27. For example, a width of proximal end 703 of the distal depression 702 is larger than the distance between the end of the first arm 106 and the end of the second arm 108 when the arms 106, 108 are substantially perpendicular to the shaft 104 of the IUD 100. Referring to FIG. 30, the proximal end 703 of the distal depression 702 has a width p.

As depicted in FIGS. 26 and 27, the loading aid 760 includes tapered walls 714, 716 that result in the distal end 705 of the distal depression 702 having a width that is narrower than the width of the proximal end 603 of the distal depression. The distal end 705 of the distal depression 702 has a minimum width sized to receive the arms 106, 108 of the IUD 100 in a collapsed or folded state (as depicted in FIG. 19). For example, the distal depression 702 is formed as a generally triangular-shaped depression that narrows to the width near the distal end 729 of tray 706. The tapered shape of distal depression 702 formed by the loading aid 760 causes the arms 106, 108 of the IUD 100 to be pushed inwards towards the shaft 104 of the IUD 100 through contact with walls 714, 716 of the loading aid 760 as the IUD 100 is pushed distally through the distal depression 702. The tray 706 supports the IUD 100 as the IUD 100 is moved distally along the distal depression 702.

The tray 706 further defines a proximal depression 704 located near the proximal end 728 of the tray 706. As depicted in FIG. 27, the proximal depression 704 is sized to accommodate an inserter handle 900 that is used to control movement of the insertion tube 202. For example, the inserter handle 900 includes a slider button 902 that can be used to control proximal and distal movement of the insertion tube 202 relative to the a rod 735 located within the insertion tube 202 and IUD 100 in order to capture and release the IUD 100 from the insertion tube 202. The rod 735 is substantially similar in construction and function to the rod 235 of the packaging system 400, except that the rod 734 includes a proximal end region that is formed for arrangement within the inserter handle 900 instead a proximal end region formed as the circular end 232.

As can be seen in FIG. 27, the proximal depression 704 has a length that is longer than the inserter handle 900, which allows the inserter handle 900 to be slid distally within the proximal depression 704 during the process of loading the IUD 100 into the insertion tube 202.

The inserter handle 900 can be detached from the tray 706 without damaging the inserter handle 900 or the tray 706. For example, the inserter handle 900 can be removed from the tray 706 once the IUD 100 is loaded into the insertion tube 202 and ready for insertion into the patient.

As depicted in FIG. 26, the system 700 can also include a protective cover 780 that can be placed over the inserter handle 900 to help prevent the inserter handle 900 from prematurely dislodging from the tray 706 and to help prevent movement of the slider button 902 during transportation, thereby protecting the inserter handle 900 from damage. The protective cover 780 can be removed from the tray 706 to expose the inserter handle 900 when a user is ready to load the IUD 100 into the insertion tube 202. In some embodiments, the protective cover 780 is molded from a transparent plastic material. The protective cover 780 has a surface profile that is generally complementary to a surface profile formed by placement of the inserter handle 900 within the proximal depression 704 of the tray 706 such that the protective cover 780 can maintain the inserter handle 900 substantially in place.

Figure 28:
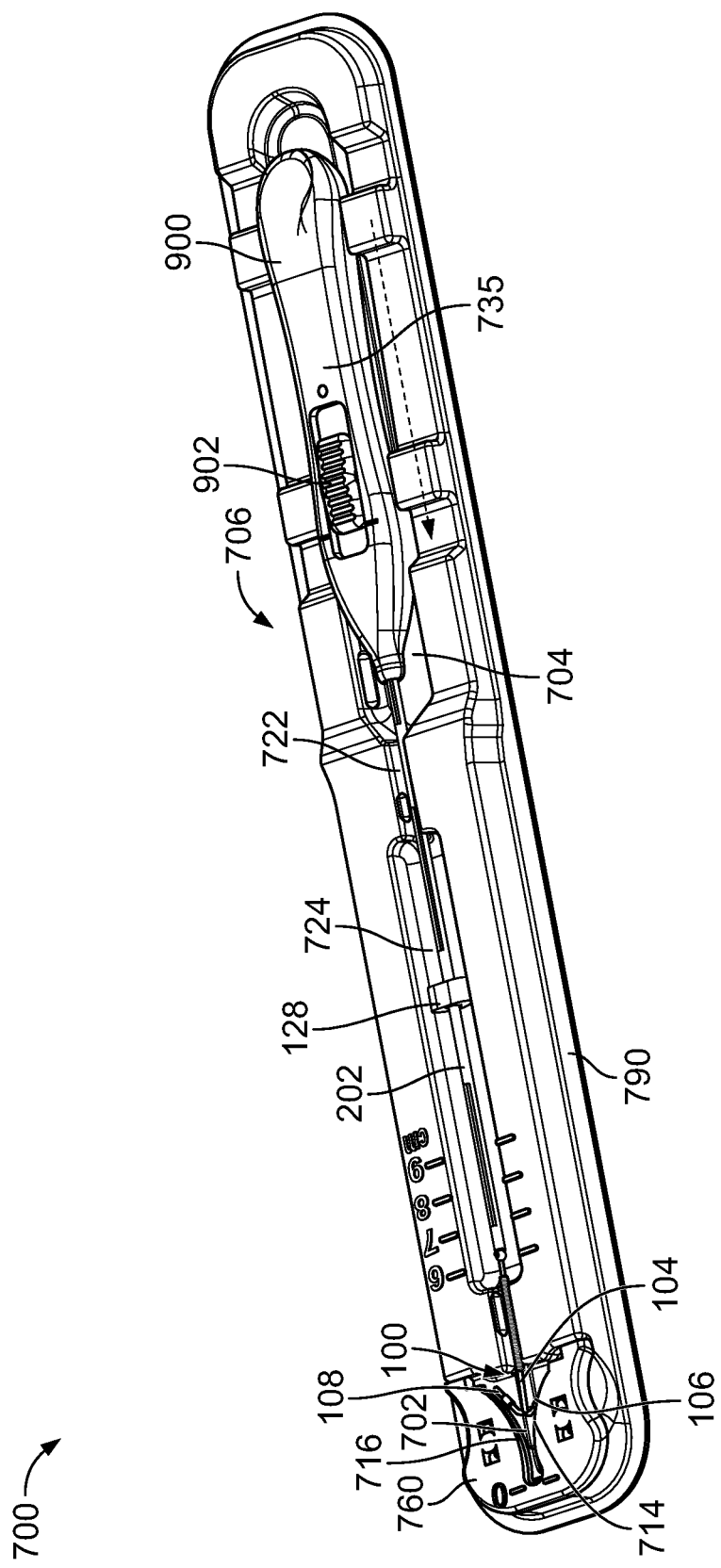
Figure 29:
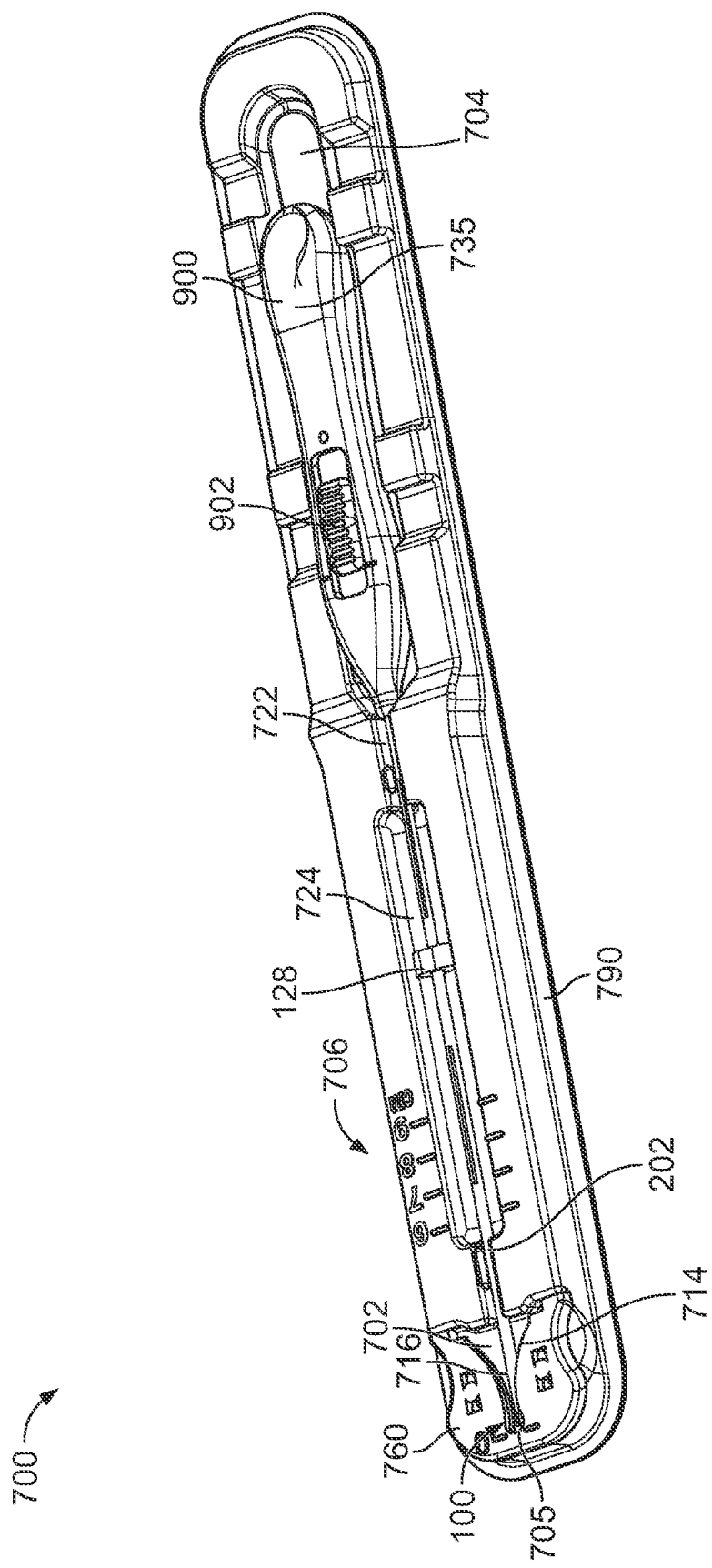

FIGS. 27-29 illustrate a method of securing the IUD 100 to the insertion tube 202 using the packaging system 700. FIG. 27 illustrates a state of the IUD 100, the insertion tube 202, and the inserter handle 900 as initially packaged in the tray 706 upon opening of the packaging system 700 by a user. The arms 106, 108 of the IUD 100 are substantially perpendicular to the shaft 104 of the IUD 100 and are positioned within the distal depression 702, with the arms 106, 108 spanning the width of the proximal end 703 of the distal depression 702. The rod 735 is positioned within the insertion tube 202 and the slider button 902 of the inserter handle 900 is in a neutral position. The insertion tube 202 is positioned within the slot 722 and is releasably coupled to the tray 706 by flanges 740, 742, 744, 746.

Referring to FIG. 28, the inserter handle 900 is advanced distally within the proximal depression 704 so that the rod 735 can be advanced distally through the insertion tube 202 towards the IUD 100 to apply a force to the end of the shaft 104 of the IUD 100 and move the IUD 100 distally within the distal depression 702. As the IUD 100 is advanced distally within the distal depression 702, the arms 106, 108 are pressed against the walls 714, 716 of the loading aid 760, which causes the arms 106, 108 of the IUD 100 to fold inwards towards the shaft 104 of the IUD 100.

Referring to FIG. 29, the handle 900 is advance distally within the proximal depression 704 until the IUD is positioned at the distal end 705 of the distal depression 702 and the arms 106, 108 of the IUD 100 are folded into a collapsed state against the shaft 104 of the IUD 100. Once the arms 106, 108 are folded against the shaft 104, the insertion tube 202 is slid distally along the slot 722 and over proximal ends of the folded arms 106, 108 of the IUD 100, as depicted in FIG. 29. For example, the slider button 902 of the inserter handle 900 can be slid distally to a forward position (e.g., by a user's finger), which causes the insertion tube 202 to slide distally over the folded arms 106, 108 of the IUD.

Once the insertion tube 202 is positioned over the folded arms 106, 108 to maintain the collapsed state of the arms 106, 108, the IUD 100, the insertion tube 202, the rod 735, and the inserter handle 900 can be removed from the tray 706 by lifting up on the inserter handle 900, and the IUD 100 is ready for implantation in the uterus 102 of a patient.

Once the IUD 100 is properly positioned within the uterus 102 of the patient (e.g., at the fundus 134 of the uterus 102, as depicted in FIG. 13), the slider button 902 of the inserter handle 900 can be drawn backwards (i.e., proximally) to a rear position to cause the insertion tube 202 to be withdrawn proximally and release the arms 106, 108 of the IUD 100 from the insertion tube 202. The rod 735 inside of the insertion tube 202 is held steady by the inserter handle 900 while the insertion tube 202 is pulled proximally to release the arms 106, 108 of the IUD 100. For example, the insertion tube 202 may be pulled proximally until the proximal end of the insertion tube 202 contacts the end portion 232 (shown in FIG. 2) of the rod 735. In some examples, the insertion tube 202 is pulled proximally by a distance of about 0.4 cm to about 0.6 cm (e.g., about 0.5 cm) to release the arms 106, 108 of the IUD 100.

In some embodiments, the inserter handle 900 includes a locking mechanism (not shown) that secures the one or more threads 110 of the IUD 100 (shown in FIG. 1) to the inserter handle 900 during loading of the IUD 100 into the insertion tube 2020 and implantation of the IUD 100 into the patient. For example, the locking mechanism of the inserter handle 900 remains closed over the threads 110 when the slider button 902 is in the neutral position or forward position (as shown in FIGS. 27-29), and only releases the threads 110 when the slider button 902 is slid proximally into the rear position (e.g., during implantation of the IUD 100 in the uterus 102 as described above). In some embodiments, the slider button 902 is designed such that it cannot be withdrawn into the rear position until it has first been pushed distally into the forward position (as shown in FIG. 29), which prevents premature release of the threads 110 of the IUD 100 from the inserter handle 900.

After ensuring proper placement of the IUD 100 in the uterus 102, the inserter handle 900 can be withdrawn proximally to remove the rod 735 and the insertion tube 202 from the cervical canal of the patient. In some examples, after removal of the insertion tube 202 from the patient, the one or more threads 110 coupled to the shaft 104 of the IUD 100 are trimmed. The threads of the IUD 100 may be trimmed so that a length of about 1.5 cm to about 2.0 cm (e.g., about 2.0 cm) of the one or more threads 110 extends out the cervical canal and into the vagina of the patient.

Figure 31:
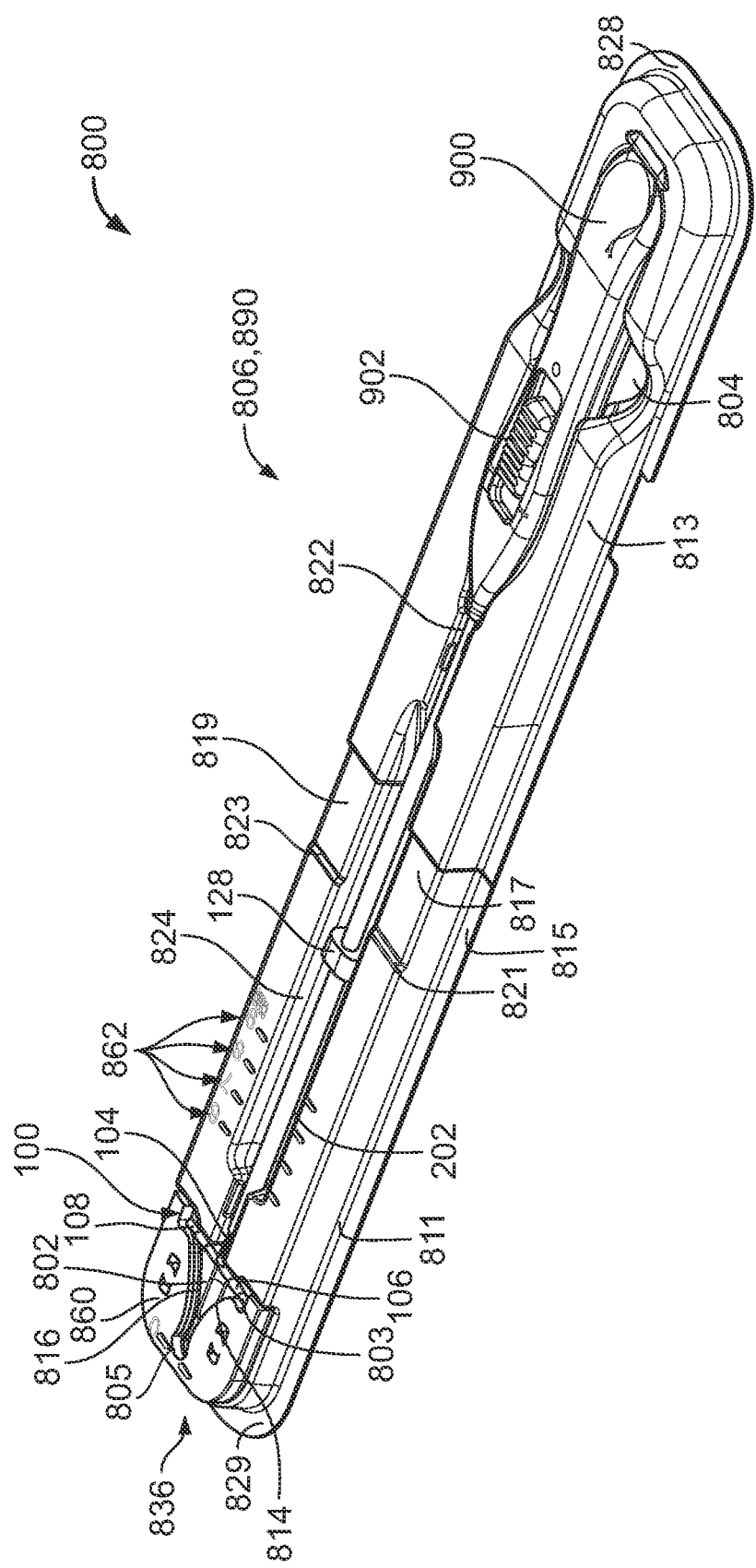
FIG. 31 is a perspective view of a packaging system for securing the IUD of FIG. 1 to the insertion tube of FIG. 2.
Figure 32:
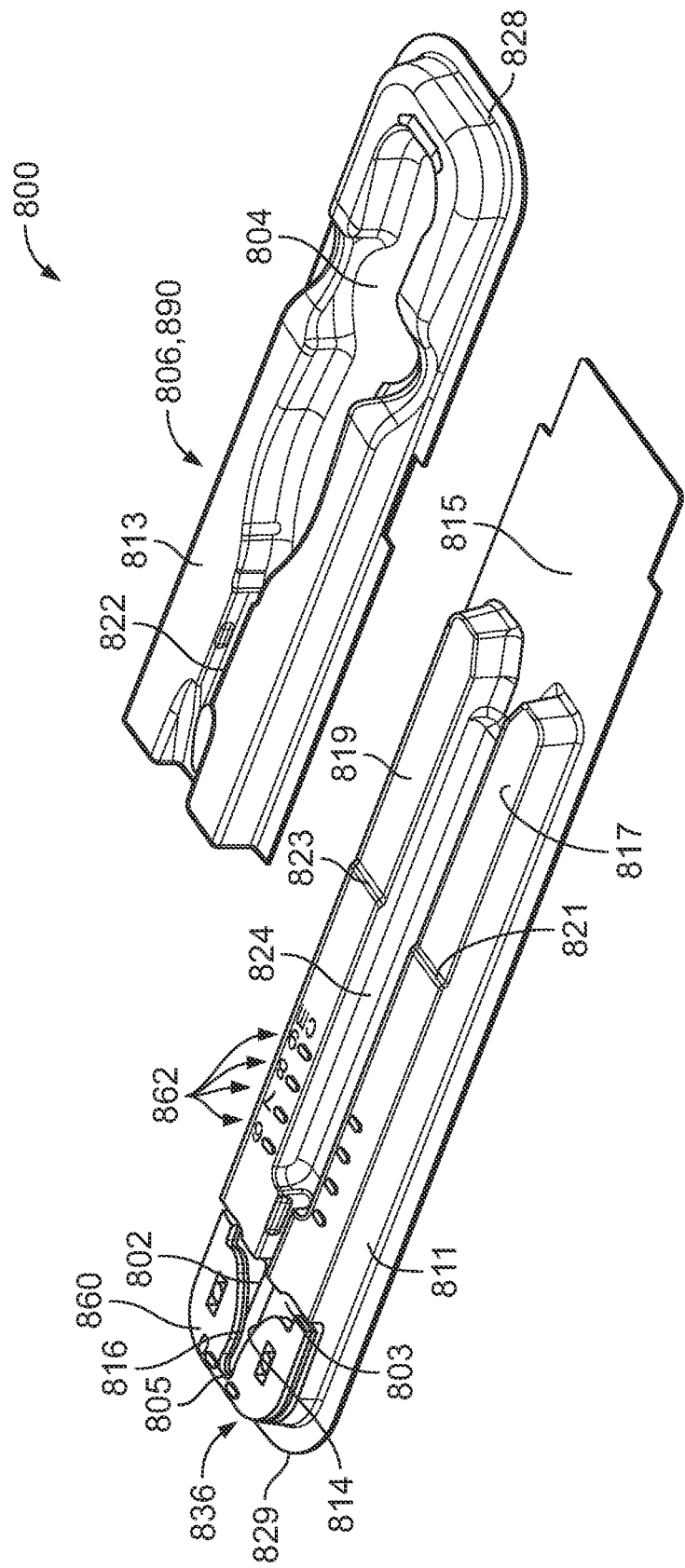
FIG. 32 is an exploded perspective view of the packaging system of FIG. 31.

FIGS. 31 and 32 depict another example packaging system 800 that includes multiple receptacles formed to facilitate folding of the arms 106, 108 of an IUD 100. For example, the packaging system 800 houses an IUD 100 and is designed for securing the IUD 100 to an insertion tube 202. The packaging system 800 includes a tray 806 defining multiple depressions formed in either of a main body 890 of the tray 806 or a loading aid 860 of the tray. The depressions include a distal depression 802, a proximal depression 804, and a slot 822 connecting the distal depression 802 and the proximal depression 804.

As depicted in FIGS. 31 and 32, the main body 890 of the tray 806 includes a first tray half 811 and a second tray half 813. In some embodiments, the first tray half 811 and the loading aid 860 are formed as two separate components that are assembled together during manufacture. In other embodiments, the two portions are provided as a single, unitary, integral component. When fully assembled, as depicted in FIG. 31, the second tray half 813 is positioned over the top of a proximal portion 815 of the first tray half 811. The second tray half 813 is slidable in the proximal and distal directions over the proximal portion 815 of the first tray half 811, which enables distal movement of the inserter handle 900 to cause folding of the arms 106, 108 of the IUD 100 for loading into the insertion tube 202. For example, as will be described in further detail herein, the second tray half 813 can be slid distally relative to the first tray half 811, which causes the inserter handle 900 and rod 735 coupled to the inserter handle 900 to be advanced distally towards the IUD 100 to apply a force to the end of the shaft 104 of the IUD 100 and move the IUD 100 distally within the distal depression 802. As the IUD 100 is advanced distally within the distal depression 802, the arms 106, 108 are pressed against the walls 814, 816 of a loading aid 860 defining the distal depression 802, which causes the arms 106, 108 of the IUD 100 to fold inwards towards the shaft 104 of the IUD 100.

As can be seen in FIGS. 31 and 32, the first tray half 811 includes two legs 817, 819 (e.g., elongate platforms) that slidably couple to two corresponding slots on the underside of the second tray half 813 by which the second tray half 813 can slide along the legs 817, 819. In addition, the first tray half 811 includes two corresponding shoulders 821, 823 (e.g., abutment surfaces) that prevent distal movement of the second tray half 813 over the first tray half 811 beyond the shoulders 821, 823. As can be seen in FIGS. 31 and 32, a height of the shoulders 821, 823 is elevated compared to that of the legs 817, 819 and to that of the second tray half 813, which prevents further distal movement of the second tray half 813.

Similar to distal depression 702 of tray 706, the first tray half 811 includes a distal depression 802 defined by a loading aid 860 coupled to the distal portion 836 of the first tray half 811. The proximal end 803 of the distal depression 802 accommodates the arms 106, 108 of the IUD 100 in an initial configuration (e.g., a packaged state) in which the arms 106, 108 are substantially perpendicular to the shaft 104 of the IUD 100, as depicted in FIG. 31. As depicted in FIGS. 31 and 32, the loading aid 860 includes tapered walls 814, 816 that result in the distal end 805 of the distal depression 802 having a width that is narrower than the width of the proximal end 803 of the distal depression. The distal end 805 of the distal depression 802 has a width d just large enough to receive the arms 106, 108 of the IUD 100 in a collapsed or folded state (as depicted in FIG. 19). That is, the distal depression 802 is formed as a generally triangular-shaped depression that narrows distally towards distal end 829 of tray 806. The shape of distal depression 802 formed by the loading aid 860 causes the arms 106, 108 of the IUD 100 to be pushed inwards towards the shaft 104 of the IUD 100 through contact with tapered walls 814, 816 of the loading aid 860 as the IUD 100 is pushed distally through the distal depression 802. The tray 806 supports the IUD 100 as the IUD 100 is moved distally along the distal depression 802.

Similar to proximal depression 704, the second tray half 813 of tray 806 defines a proximal depression 804 located near the proximal end 828 of the tray 806. As depicted in FIG. 31, the proximal depression 804 is sized to accommodate the inserter handle 900 and has a length that is slightly larger than the length of the inserter handle 900, which prevents the inserter handle 900 from prematurely moving out of the tray 806 during transportation of the system 800 and loading of the IUD 100 into the insertion tube 202.

As depicted in FIG. 31, the slot 822 accommodates an insertion tube 202 and restricts lateral movement and angular movement of the insertion tube 202 outside the slot 822. As depicted in FIGS. 31 and 32, the slot 822 can include a gripping region 824 that is wider than the rest of the slot 722 (e.g., similar to gripping region 724 of tray 706 depicted in FIGS. 26 and 27). The gripping region 824 provides space for a user to grasp a cervical collar 128 that is slidably coupled to of the insertion tube 202 and positioned within the gripping region 824 when the insertion tube 202 is positioned within the slot 822. As can be seen in FIGS. 31 and 32, the first tray half 811 can include markings 862 indicating positions to position the cervical collar 128 according to a measured uterine depth, as discussed above with respect to the tray 706.

A method of securing the IUD 100 to the insertion tube 202 using the packaging system 800 will be described with reference to FIGS. 31 and 32. Referring to FIG. 31, the arms 106, 108 of the IUD 100 are substantially perpendicular to the shaft 104 of the IUD 100 and are positioned within the distal depression 802, with the arms 106, 108 spanning the width of the proximal end 803 of the distal depression 802 in an initial configuration of the packaging system 800. The rod 735 is positioned within the insertion tube 202, and the inserter handle 900 is positioned within the proximal depression 804. The slider button 902 of the inserter handle 900 is in a neutral position. The insertion tube 202 is positioned within the slot 822.

The second tray half 813 is slid distally along the leg 817, 819 of the first tray half 811 so that the inserter handle 900 and rod 735 coupled to the handle 900 are advanced distally towards the IUD 100. For example, a user can hold the first tray half 811 still while sliding the second tray half 813 distally over the proximal portion 815 of the first tray half 811 using his or her fingers. As the rod 735 is advanced distally via distal movement of second tray half 813, the rod 735 applies a force to the end of the shaft 104 of the IUD 100 to move the IUD 100 distally within the distal depression 802. As the IUD 100 is advanced distally within the distal depression 802, the arms 106, 108 are pressed against the loading aid 860, which causes the arms 106, 108 of the IUD 100 to fold inwards towards the shaft 104 of the IUD 100.

The second tray half 813 is slid distally along the legs 817, 819 of the first tray half 811 until the second tray half 813 abuts the shoulders 821, 823 of the first tray half 811, which corresponds to the IUD 100 being positioned at the distal end 805 of the distal depression 802 and the arms 106, 108 of the IUD 100 being folded into a collapsed state against the shaft 104 of the IUD 100. Once the arms 106, 108 are folded against the shaft 104, the insertion tube 202 is slid distally along the slot 822 and over proximal ends of the folded arms 106, 108. For example, the slider button 902 of the inserter handle 900 can be slid distally to a forward position, which causes the insertion tube 202 to slide distally over the folded arms 106, 108 of the IUD.

Once the insertion tube 202 is positioned over the folded arms 106, 108 of the IUD 100 to maintain the collapsed state of the arms 106, 108, the IUD 100, insertion tube 202, rod 735, and inserter handle 900 can be removed from the tray 806 by lifting up on the inserter handle 900, and the IUD 100 can be implanted in the uterus 102 of a patient, as described above.

While the packaging systems 200, 500, 700, 800; the loading devices 204, 504, 604; and the trays 406, 706, 806 have been described and illustrated with respect to certain dimensions, sizes, shapes, arrangements, materials, and methods, in some embodiments, a packaging system, a loading device, or a tray that is otherwise substantially similar in construction and function to any of the packaging systems 200, 500, 700, 800; the loading devices 204, 504, 604; or the trays 406, 706, 806 may include one or more different dimensions, sizes, shapes, arrangements, and materials or may be utilized according to different methods. Accordingly, other embodiments are within the scope of the following claims.

What is claimed is:

1. A tray for securing an implantable device to a carrier member, the tray defining:
    a slot configured to retain the carrier member, wherein the carrier member surrounds a shaft of the implantable device; and
    a receptacle adjacent the slot, wherein the receptacle has a first width at a proximal end of the receptacle to receive first and second arms of the implantable device in an initial state in which the first and second arms extend substantially perpendicularly from the shaft, wherein the receptacle has a second width at a distal end of the receptacle for receiving the first and second arms of the implantable device in a collapsed state in which the first and second arms are folded against the shaft such that the carrier member can be slid over the first and second arms to retain the first and second arms, and wherein the second width is less than the first width.

2. The tray of claim 1, wherein the tray defines one or more flanges configured to secure the carrier member to the tray.

3. The tray of claim 1, wherein the tray comprises:
    a main body defining the slot; and
    a loading aid defining the receptacle, the loading aid being coupled to a distal portion of the main body.

4. The tray of claim 3, wherein the loading aid comprises a first wall and a second wall opposite the first wall, and wherein the first and second walls are formed to guide the first and second arms of the implantable device into the collapsed state upon distal movement of the implantable device within the receptacle.

5. The tray of claim 4, wherein the receptacle has a tapered shape.

6. The tray of claim 1, wherein the implantable device comprises an intrauterine device, and wherein the carrier member comprises an insertion tube.

7. The tray of claim 1, wherein the receptacle is a first receptacle, and wherein the tray further defines a second receptacle adjacent the slot and opposite the first receptacle, the second receptacle being configured to receive a handle that is coupled to the carrier member.

8. The tray of claim 7, wherein the second receptacle is longer than the handle to permit distal movement of the handle within the second receptacle.

9. The tray of claim 1, further defining a gripping region positioned along the slot, the gripping region being wider than the slot.

10. The tray of claim 9, wherein the tray comprises ruler markings adjacent the gripping region, the ruler markings indicating respective uterine depths.

11. The tray of claim 1, wherein the tray comprises:
    a first support body defining the receptacle; and
    a second support body slidably coupled to the first support body.

12. The tray of claim 11, wherein the first support body defines:
    an elongate platform slidably coupled to the second support body; and
    a shoulder configured to prevent distal movement of the second support body relative to the first support body beyond the shoulder.

13. The tray of claim 11, wherein distal movement of the second support body relative to the first support body causes the implantable device to move distally within the receptacle from the proximal end of the receptacle to the distal end of the receptacle to cause the first and second arms of the implantable device to move from the initial state into the collapsed state.

14. A packaging system comprising:
    a tray for securing an implantable device to a carrier member, the tray comprising:
        a slot configured to retain the carrier member, wherein the carrier member surrounds a shaft of the implantable device, and
        a receptacle adjacent the slot, wherein the receptacle has a first width at a proximal end of the receptacle to receive first and second arms of the implantable device in an initial state in which the first and second arms extend substantially perpendicularly from the shaft, wherein the receptacle has a second width at a distal end of the receptacle for receiving the first and second arms of the implantable device in a collapsed state in which the first and second arms are folded against the shaft such that the carrier member can be slid over the first and second arms to retain the first and second arms, and wherein the second width is less than the first width; and
    a protective cover formed complementary to at least a portion of the tray for securing a handle that is coupled to the carrier member to the tray.

15. The packaging system of claim 14, wherein the tray defines one or more flanges configured to secure the carrier member to the tray.

16. The packaging system of claim 14, wherein the tray comprises:
    a main body defining the slot; and
    a loading aid defining the receptacle, the loading aid being coupled to a distal portion of the main body.

17. The packaging system of claim 16, wherein the loading aid comprises a first wall and a second wall opposite the first wall, and wherein the first and second walls are formed to guide the first and second arms of the implantable device into the collapsed state upon distal movement of the implantable device within the receptacle.

18. The packaging system of claim 17, wherein the receptacle has a tapered shape.

19. The packaging system of claim 14, further defining a gripping region positioned along the slot, the gripping region being wider than the slot.

20. A method of preparing an implantable device for deployment, the method comprising:
    accessing a tray that is assembled with the implantable device and with a carrier member that surrounds a shaft of the implantable device, the tray defining:

a slot configured to retain the carrier member, wherein the carrier member surrounds the shaft of the implantable device, and a receptacle adjacent the slot, wherein the receptacle has a first width at a proximal end of the receptacle to receive first and second arms of the implantable device in an initial state in which the first and second arms extend substantially perpendicularly from the shaft of the implantable device, wherein the receptacle has a second width at a distal end of the receptacle for receiving the first and second arms of the implantable device in a collapsed state in which the first and second arms are folded against the shaft, and wherein the second width is less than the first width;

moving the implantable device distally from the proximal end of the receptacle to the distal end of the receptacle, causing the first and second arms of the implantable device to move from the initial state to the collapsed state; and sliding the carrier member distally along the slot and over the first and second arms to retain the first and second arms within the carrier member.

* * * * *